United States Patent
Satoh et al.

(10) Patent No.: US 6,916,837 B2
(45) Date of Patent: Jul. 12, 2005

(54) AMIDINO DERIVATIVES AND ANTICOAGULANTS AND THROMBOSIS THERAPEUTIC AGENTS CONTAINING THEM

(75) Inventors: Takashi Satoh, Tsukuba (JP); Yasushi Okamoto, Ibaraki (JP); Osamu Asano, Ushiku (JP); Nobuhisa Watanabe, Tsukuba (JP); Tadashi Nagakura, Ushiku (JP); Takao Saeki, Moriya (JP); Atsushi Inoue, Tsukuba (JP); Masahiro Sakurai, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 294 days.

(21) Appl. No.: 10/294,198

(22) Filed: Nov. 14, 2002

(65) Prior Publication Data

US 2003/0181766 A1 Sep. 25, 2003

(30) Foreign Application Priority Data

Nov. 15, 2001 (JP) .................................... P2001-350637

(51) Int. Cl.[7] ...................... A61K 31/415; A61K 31/38; A61K 31/36; A61K 31/21; A61K 31/24

(52) U.S. Cl. ...................... 514/398; 514/399; 514/445; 514/466; 514/510; 514/535; 514/562; 548/217; 548/323.5; 548/324.1; 549/65; 549/76; 549/77; 560/13; 562/427; 562/439

(58) Field of Search ................................... 514/398, 399, 514/445, 466, 510, 535, 562; 548/217, 323.5, 324.1; 549/65, 76, 77; 560/13; 562/427, 439

(56) References Cited

FOREIGN PATENT DOCUMENTS

| EP | 1 078 917 A1 | 2/2001 |
|----|---|---|
| WO | WO 98/01422 | 1/1998 |
| WO | WO99/41231 | 8/1999 |
| WO | WO 00/58346 | 10/2000 |
| WO | WP 00/66545 | 11/2000 |
| WO | WP 01/19788 A2 | 3/2001 |

OTHER PUBLICATIONS

Patrick Roussel. et al., Inhibition of the Tissue Factor/Factor VIIa Complex–Lead Optimization Using Combinatorial Chemistry. Tetrahedron 55 (1999) 6219–6230.

*Primary Examiner*—Brian Davis
(74) *Attorney, Agent, or Firm*—Brenda Herschbach Jarrell; Charles E. Lyon; Choate, Hall & Stewart LLP

(57) ABSTRACT

Amidino derivatives represented by the following general formula (I):

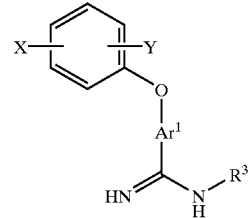

{where X is a group represented by $R^1SO_2NR^2$— (wherein $R^1$ represents optionally substituted $C_{6-14}$ aryl, etc. and $R^2$ represents hydrogen atom, etc.), etc., $Ar^1$ represents 2,6-naphthylene, etc., $R^3$ represents hydrogen atom, etc. and Y represents carboxyphenyl, etc.}
and their pharmacologically acceptable salts or solvates.

16 Claims, No Drawings

AMIDINO DERIVATIVES AND ANTICOAGULANTS AND THROMBOSIS THERAPEUTIC AGENTS CONTAINING THEM

BACKGROUND OF THE INVENTION

1. Field of the Invention

The present invention relates to medicinally useful novel amidino derivatives, to their pharmacologically acceptable salts or solvates, and to blood clotting factor VIIa inhibitors, anticoagulants and thrombosis therapeutic agents containing them as active ingredients.

2. Related Background Art

Destruction of blood vessels in the body triggers rapid production of thrombin to prevent death by bleeding. On the other hand, overproduction of thrombin accompanying inflammation reaction at damaged blood vessels leads to thrombosis, which impairs the functioning of important organs. Thrombin inhibitors such as heparin and warfarin, which inhibit thrombin production or directly inhibit thrombin activity, have long been used as anticoagulants for treatment or prevention of thrombosis. However, because such drugs have not been very satisfying from a therapeutic standpoint, research and development have been pursued on a worldwide scale for new anticoagulants with excellent dose response, low risk of hemorrhage and suitability for oral administration.

Incidentally, mechanisms of blood clotting had been divided into two types, of the "intrinsic coagulation pathway" which is initiated by activation of Factor XII (FXII) by contact with negatively charged substances, or of the "extrinsic coagulation pathway" which is activated by Tissue Factor (TF) and Factor VII (FVII). It is extrinsic coagulation that is implicated in thrombosis because of specific expression of TF observed in the clinical condition. In the blood clotting cascade, compounds that inhibit blood clotting factor VIIa, which is furthest upstream in the extrinsic coagulation pathway, are believed to be useful as prophylactic and/or therapeutic agents for clinical conditions involving thrombogenesis in which extrinsic clotting mechanisms are implicated. In addition, blood clotting factor VIIa inhibitors, unlike thrombin inhibitors, are expected to produce milder hemorrhage since the intrinsic coagulation pathway still remains, and are thus believed to be useful from this viewpoint as well.

Such compounds that have been conventionally known to inhibit blood clotting factor VIIa include amidinonaphthol derivatives, (Tetrahedron, Vol. 55, p. 6219, 1999), amidino derivatives (International Publication No. WO99/41231), N-sulfonyl dipeptide derivatives (International Publication No. WO00/58346), 6-[[(allyl)oxy]methyl]naphthalene-2-carboximidamide derivatives (International Publication No. WO00/66545), and the like.

However, none of the publicly known compounds of the prior art have given satisfactory results in terms of inhibiting activity against blood clotting factor VIIa.

SUMMARY OF THE INVENTION

It is an object of the present invention, which has been accomplished in light of the aforementioned problems of the prior art, to provide novel amidino derivatives having serine protease inhibiting activity and especially excellent inhibiting activity against blood clotting factor VIIa, as well as their pharmacologically acceptable salts or solvates, and blood clotting factor VIIa inhibitors, anticoagulants and thrombosis therapeutic agents containing them.

As a result of avid research directed toward achieving the object stated above, the present inventors have completed the invention upon discovering that novel amidino derivatives having a specific chemical structure exhibit excellent inhibiting activity against blood clotting factor VIIa.

Specifically, the present invention provides:

<1> An amidino derivative represented by the following general formula (I):

{where X represents $C_{1-6}$ alkyl, a halogen atom, $-NH_2$ or a group represented by the following formula:

(where $R^1$ represents optionally substituted $C_{1-6}$ alkyl, optionally substituted $C_{1-6}$ alkoxy, optionally substituted $C_{3-8}$ cycloalkyl, optionally substituted $C_{6-14}$ aryl, optionally substituted $C_{7-20}$ aralkyl, an optionally substituted 5- to 14-membered aromatic heterocyclic group or a group represented by the following formula:

(where $R^4$ represents hydrogen atom, $C_{1-6}$ alkyl or optionally substituted $C_{2-7}$ acyl),
$R^2$ represents hydrogen atom or $C_{1-6}$ alkyl, and
$X^2$ represents $-CO-$, $-SO_2-$, $-NH-CO-$ or a single bond),
$R^3$ represents hydrogen atom, hydroxyl, $C_{2-7}$ acyl or $C_{2-7}$ alkoxycarbonyl,
Y represents a group of the formula $-Ar^2-CO_2R^5$ (where $Ar^2$ represents optionally substituted $C_{6-14}$ aryl, an optionally substituted 5- to 14-membered aromatic heterocyclic group or a single bond and $R^5$ represents hydrogen atom or $C_{1-6}$ alkyl), and
$Ar^1$ represents 2,6-naphthylene, 1,4-phenylene, 1,3-phenylene, a group represented by the following formula:

or a group represented by the following formula:

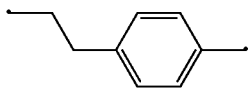

or a pharmacologically acceptable salt or solvate thereof.

<2> An amidino derivative represented by the following general formula (II):

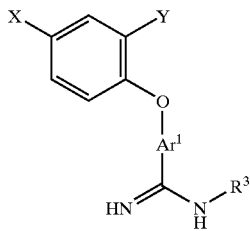

(where X, Y, Ar$^1$ and R$^3$ have the same definitions as X, Y, Ar$^1$ and R$^3$ in <1>),
or a pharmacologically acceptable salt or solvate thereof.

<3> An amidino derivative represented by the following general formula (III):

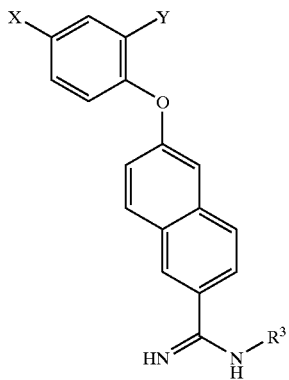

(where X, Y and R$^3$ have the same definitions as X, Y and R$^3$ in <1>),
or a pharmacologically acceptable salt or solvate thereof.

<4> An amidino derivative or a pharmacologically acceptable salt or solvate thereof according to any one of <1> to <3> above wherein R$^3$ is hydrogen atom.

<5> An amidino derivative or a pharmacologically acceptable salt or solvate thereof according to any one of <1> to <4> above wherein X is C$_{1-6}$ alkyl or a group represented by the formula R$^1$—SO$_2$NH— (where R$^1$ has the same definition as R$^1$ in <1>).

<6> An amidino derivative or a pharmacologically acceptable salt or solvate thereof according to any one of <1> to <5> above wherein X is a group represented by the formula R$^1$—SO$_2$NH— {where R$^1$ represents optionally substituted C$_{6-14}$ aryl or a group represented by the following formula:

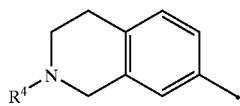

(where R$^4$ represents optionally substituted C$_{2-7}$ acyl)}.

<7> An amidino derivative or a pharmacologically acceptable salt or solvate thereof according to any one of <1> to <6> above wherein Y is carboxyl or optionally substituted carboxyphenyl.

<8> An amidino derivative or a pharmacologically acceptable salt or solvate thereof according to any one of <1> to <7> above wherein Y is a group represented by the following formula:

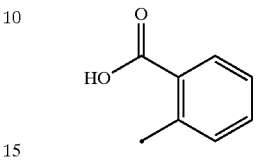

<9> An amidino derivative or a pharmacologically acceptable salt or solvate thereof according to <1>, wherein X represents C$_{1-6}$ alkyl, a halogen atom, —NH$_2$ or a group represented by the following formula:

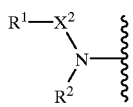

{where R$^1$ represents C$_{1-6}$ alkyl, C$_{1-6}$ alkoxy, C$_{3-8}$ cycloalkyl, C$_{6-14}$ aryl, C$_{7-20}$ aralkyl, a 5- to 14-membered aromatic heterocyclic group or a group represented by the following formula:

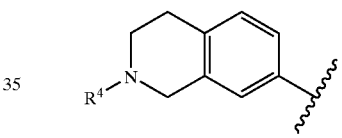

(where R$^4$ represents hydrogen atom, C$_{1-6}$ alkyl or C$_{2-7}$ acyl) and R$^1$ optionally has 1–3 substituents selected from the following substituent group A,
R$^2$ represents hydrogen atom or C$_{1-6}$ alkyl, and
X$^2$ represents —CO—, —SO$_2$—, —NH—CO— or a single bond}.

(Substituent Group A)
The group consisting of halogen atoms, C$_{1-6}$ alkyl, C$_{1-6}$ alkoxy, C$_{1-6}$ alkylsulfonyl, C$_{3-8}$ cycloalkyl, C$_{3-8}$ cycloalkoxy, halo C$_{1-6}$ alkyl, halo C$_{1-6}$ alkoxy, C$_{6-14}$ aryl, C$_{1-6}$ alkoxy-C$_{6-14}$ aryl, C$_{6-14}$ aryloxy, C$_{6-14}$ arylsulfonyl, nitro, C$_{1-6}$ alkoxycarbonyl, carboxyl, acetamide, hydroxyl, 5- to 14-membered aromatic heterocyclic groups, CF$_3$—, CF$_3$O—, Z—CO— {where Z represents —NR$^7$R$^8$ (wherein R$^7$ and R$^8$ may be the same or different and each represents hydrogen atom, C$_{1-6}$ alkyl, C$_{3-8}$ cycloalkyl, C$_{6-14}$ aryl, benzyl or C$_{3-8}$ cycloalkylmethyl), 1-pyrrolidinyl or 1-piperidyl}, amino C$_{1-6}$ alkyl and C$_{1-6}$ alkylenedioxy.

<10> An amidino derivative or a pharmacologically acceptable salt or solvate thereof according to <9>, wherein substituent group A is the group consisting of halogen atoms, C$_{1-6}$ alkyl, C$_{1-6}$ alkoxy, C$_{1-6}$ alkylsulfonyl, halo C$_{1-6}$ alkyl, halo C$_{1-6}$ alkoxy, C$_{6-14}$ arylsulfonyl, nitro, carboxyl, acetamide, Z—CO— {where Z represents —NR$^7$R$^8$ (wherein R$^7$ and R$^8$ may be the same or different and each represents hydrogen atom or C$_{1-6}$ alkyl)} and C$_{1-6}$ alkylenedioxy.

<11> An amidino derivative or a pharmacologically acceptable salt or solvate thereof according to <1>, wherein Y represents a group represented by the formula —Ar³—CO₂R⁵ (where Ar³ represents $C_{6-14}$ aryl or a 5- to 14-membered aromatic heterocyclic group, and R⁵ represents hydrogen atom or $C_{1-6}$ alkyl) or a group represented by the formula —CO₂R⁵ (wherein R⁵ has the same definition as above), and Ar³ optionally has 1–3 substituents selected from the following substituent group B.
(Substituent Group B)

The group consisting of halogen atoms, $C_{1-6}$ alkyl, $C_{1-6}$ alkoxy, $C_{1-6}$ alkylsulfonyl, $C_{3-8}$ cycloalkyl, $C_{3-8}$ cycloalkoxy, halo $C_{1-6}$ alkyl, halo $C_{1-6}$ alkoxy, $C_{6-14}$ aryl, $C_{1-6}$ alkoxy-$C_{6-14}$ aryl, $C_{6-14}$ aryloxy, $C_{6-14}$ arylsulfonyl, nitro, $C_{1-6}$ alkoxycarbonyl, carboxyl, acetamide, hydroxyl, 5- to 14-membered aromatic heterocyclic groups, CF₃—, CF₃O—, Z—CO— {where Z represents —NR⁷R⁸ (wherein R⁷ and R⁸ may be the same or different and each represents hydrogen atom, $C_{1-6}$ alkyl, $C_{3-8}$ cycloalkyl, $C_{6-14}$ aryl, benzyl or $C_{3-8}$ cycloalkylmethyl), 1-pyrrolidinyl or 1-piperidyl}, amino $C_{1-6}$ alkyl and $C_{1-6}$ alkylenedioxy.

<12> An amidino derivative or a pharmacologically acceptable salt or solvate thereof according to <11>, wherein substituent group B is the group consisting of halogen atoms, $C_{1-6}$ alkyl, $C_{1-6}$ alkoxy, $C_{1-6}$ alkylsulfonyl, halo $C_{1-6}$ alkyl, halo $C_{1-6}$ alkoxy, $C_{6-14}$ arylsulfonyl, nitro, carboxyl, acetamide, Z—CO— {where Z represents —NR⁷R⁸ (wherein R⁷ and R⁸ may be the same or different and each represents hydrogen atom or $C_{1-6}$ alkyl) and $C_{1-6}$ alkylenedioxy.

<13> A blood clotting factor VIIa inhibitor comprising an amidino derivative or a pharmacologically acceptable salt or solvate thereof according to any one of <1> to <8>.

<14> An anticoagulant containing, as an active ingredient, an amidino derivative or a pharmacologically acceptable salt or solvate thereof according to any one of <1> to <8>.

<15> A thrombosis therapeutic agent containing, as an active ingredient, an amidino derivative or a pharmacologically acceptable salt or solvate thereof according to any one of <1> to <8>.

<16> A compound library comprising an amidino derivative or a pharmacologically acceptable salt or solvate thereof according to any one of <1> to <8>.

<17> A compound library comprising 1 to 1 million (preferably 8 to 1 million, more preferably 16 to 1 million and even more preferably 96 to 1 million) amidino derivatives or their pharmacologically acceptable salts or solvates thereof according to any of <1> to <8>.

<18> The use of an amidino derivative or a pharmacologically acceptable salt or solvate thereof according to any one of <1> to <8> as a blood clotting factor VIIa inhibitor.

<19> The use of an amidino derivative or a pharmacologically acceptable salt or solvate thereof according to any one of <1> to <8> as an active ingredient of an anticoagulant.

<20> The use of an amidino derivative or a pharmacologically acceptable salt or solvate thereof according to any one of <1> to <8> as an active ingredient of a thrombosis therapeutic agent.

<21> A treatment method for clinical conditions involving thrombogenesis in which extrinsic blood clotting mechanisms are implicated, which involves administering an amidino derivative or a pharmacologically acceptable salt or solvate thereof according to any one of <1> to <8>.

<22> A prophylactic method for clinical conditions involving thrombogenesis in which extrinsic blood clotting mechanisms are implicated, which involves administering an amidino derivative or a pharmacologically acceptable salt or solvate thereof according to any one of <1> to <8>.

DESCRIPTION OF THE PREFERRED EMBODIMENTS

The present invention will now be explained in further detail. First, the amidino derivatives of the invention and their pharmacologically acceptable salts or solvates will be explained.

The amidino derivatives of the invention are represented by general formula (I) given above. There are no particular restrictions on the positions of the group represented by X and the group represented by Y bonded to the benzene ring in general formula (I), but for more enhanced pharmacological activity, preferably an ether bond is formed at the carbon atom at position 2 of the Y-substituted benzene (where the Y-bonded benzene carbon atom is position 1) and a group represented by X is bonded at the carbon atom at position 4 or 5 (most preferably position 5). Preferred, therefore, are amidino derivatives represented by the following general formula (II):

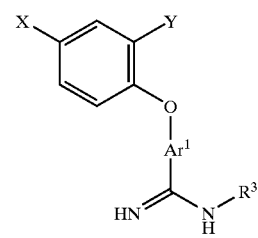

(where X, Y, Ar¹ and R³ have the same definitions as X, Y, Ar¹ and R³ for general formula (I)), or pharmacologically acceptable salts or solvates thereof.

The group represented by Ar¹ in general formula (I) is 2,6-naphthylene, 1,4-phenylene, 1,3-phenylene, a group represented by the following formula:

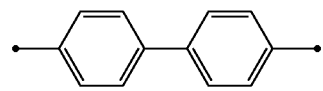

or a group represented by the following formula:

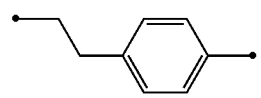

and for more enhanced pharmacological activity it is preferably 2,6-naphthylene. Preferred, therefore, are amidino derivatives represented by the following general formula (III):

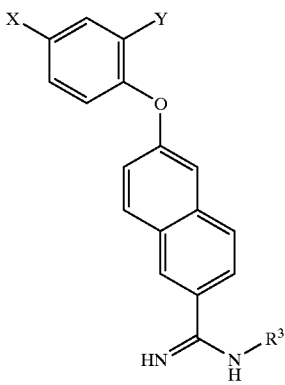

(where X, Y and R³ have the same definitions as X, Y, and R³ for general formula (I)),
or pharmacologically acceptable salts or solvates thereof.

Also, X in general formula (I) is $C_{1-6}$ alkyl, a halogen atom, —$NH_2$ or a group represented by the following formula (IV):

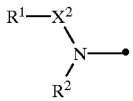

{where R¹ represents optionally substituted $C_{1-6}$ alkyl, optionally substituted $C_{1-6}$ alkoxy, optionally substituted $C_{3-8}$ cycloalkyl, optionally substituted $C_{6-14}$ aryl, optionally substituted $C_{7-20}$ aralkyl, an optionally substituted 5- to 14-membered aromatic is heterocyclic group or a group represented by the following formula (V):

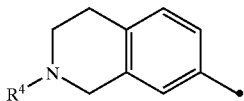

(where R⁴ represents hydrogen atom, $C_{1-6}$ alkyl or optionally substituted $C_{2-7}$ acyl),
R² represents hydrogen atom or $C_{1-6}$ alkyl, and
X² represents —CO—, —$SO_2$—, —NH—CO— or a single bond}, but for more enhanced pharmacological activity it is preferably $C_{1-6}$ alkyl or a group represented by the aforementioned formula (IV) (for example, R¹—NHCONR²—, R¹—CONR²—, R¹—$SO_2NR^2$—), more preferably $C_{1-6}$ alkyl (especially methyl) or R¹—$SO_2NR^2$—, and most preferably R¹—$SO_2NR^2$—.

The group represented by X² in general formula (IV) is —CO—, —$SO_2$—, —NH—CO— or a single bond, but for more enhanced pharmacological activity it is preferably —CO—, —$SO_2$— or —NH—CO—, and most preferably —$SO_2$—.

The group represented by R¹ in general formula (IV) is (i) optionally substituted $C_{1-6}$ alkyl, (ii) optionally substituted $C_{1-6}$ alkoxy, (iii) optionally substituted $C_{3-8}$ cycloalkyl, (iv) optionally substituted $C_{6-14}$ aryl, (v) optionally substituted $C_{7-20}$ aralkyl, (vi) an optionally substituted 5- to 14-membered aromatic heterocyclic group or (vii) a group represented by formula (V) above, and it is preferably (i), (iii), (iv), (v), (vi) or (vii); for more enhanced pharmacological activity it is most preferably (iv) or (vii).

The group represented by R⁴ in formula (V) above is hydrogen atom, $C_{1-6}$ alkyl or optionally substituted $C_{2-7}$ acyl, but for more enhanced pharmacological activity it is preferably optionally substituted $C_{2-7}$ acyl.

The group represented by R² in formula (IV) above is hydrogen atom or $C_{1-6}$ alkyl, but for more enhanced pharmacological activity it is preferably hydrogen atom.

The group represented by R³ in general formula (I) is hydrogen atom, hydroxyl, $C_{2-7}$ acyl or $C_{2-7}$ alkoxycarbonyl, but for more enhanced pharmacological activity it is preferably hydrogen atom.

The group represented by Y in general formula (I) is a group represented by the formula —Ar²—COOR⁵ (where Ar² represents optionally substituted $C_{6-14}$ aryl, an optionally substituted 5- to 14-membered aromatic heterocyclic group or a single bond, and R⁵ represents hydrogen atom or $C_{1-6}$ alkyl). For more enhanced pharmacological activity, the group represented by Y is preferably a carboxyl group (—COOH) or a group represented by the formula —Ar²—COOH (where Ar² represents optionally substituted $C_{6-14}$ aryl), more preferably carboxyl or optionally substituted carboxyphenyl, and most preferably a group represented by the following formula:

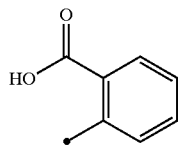

The term "$C_{1-6}$ alkyl" used throughout the present specification refers to a linear or branched alkyl group of 1–6 carbons (preferably 1–4 carbons), such as methyl, ethyl, n-propyl, i-propyl, n-butyl, s-butyl, t-butyl, pentyl, isopentyl, hexyl or the like.

The term "$C_{1-6}$ alkoxy" refers to a linear or branched alkoxy group of 1–6 carbons (preferably 1–4 carbons), such as methoxy, ethoxy, n-propoxy, i-propoxy, n-butoxy, s-butoxy, t-butoxy, pentoxy, isopentoxy, hexoxy or the like.

The term "$C_{3-8}$ cycloalkyl" refers to a cyclic saturated hydrocarbon group of 3–8 carbons (preferably 3–6 carbons) such as cyclopropyl, cyclobutyl, cyclopentyl, cyclohexyl, cycloheptyl, cyclooctyl or the like.

The term "$C_{6-14}$ aryl" refers to a monovalent aromatic hydrocarbon group of 6–14 carbons (preferably 6–10 carbons) lacking one of its hydrogen atoms, such as phenyl, biphenyl, naphthyl, anthranyl, phenanthryl, tolyl, xylyl or the like, with phenyl and naphthyl being preferred for more enhanced pharmacological activity. The $C_{6-14}$ aryl group referred to here need not necessarily be monovalent, and it may be a divalent group lacking yet another hydrogen atom.

The term "$C_{7-20}$ aralkyl" refers to a group which is an alkyl group substituted with an aryl group at one of its hydrogen atoms, and has 7–20 (preferably 7–14) carbons, such as benzyl, phenethyl or the like.

The term "5- to 14-membered aromatic heterocyclic group" refers to a 5- to 14-membered aromatic heterocyclic group having at least one hetero atom (nitrogen atom, oxygen atom, sulfur atom, etc.), such as thienyl, pyridyl, imidazolyl, pyrazinyl, pyrimidyl or the like. The 5- to 14-membered aromatic heterocyclic group referred to here need necessarily not be monovalent, and it may be a divalent group lacking yet another hydrogen atom.

The term "$C_{2-7}$ acyl", refers to a carbonyl group substituted with an alkyl group, aryl group, alkoxy group, etc. and having 2–7 carbons, and is preferably a carbonyl group bonded to a $C_{1-6}$ alkyl group. Examples of such $C_{2-7}$ acyl groups include alkylcarbonyl groups such as acetyl, propionyl, butanoyl, pivaloyl and cyclohexanecarbonyl and arylcarbonyl groups such as benzoyl, among which acetyl, propionyl and butanoyl are preferred.

The term "$C_{2-7}$ alkoxycarbonyl" refers to a carbonyl group bonded to a $C_{1-6}$ alkoxy group as defined above and having 2–7 carbons, such as methoxycarbonyl, ethoxycarbonyl or the like.

The term "halogen atom" refers to a fluorine atom, chlorine atom, bromine atom or iodine atom.

The term "optionally substituted" as used throughout the present specification means "optionally having one or more substituents in any desired combination at substitutable positions". As specific such substituents there may be mentioned hydrogen atom, halogen atoms (fluorine, chlorine, bromine and iodine), $C_{1-6}$ alkyl, $C_{1-6}$ alkoxy, $C_{1-6}$ alkylsulfonyl, $C_{3-8}$ cycloalkyl, $C_{3-8}$ cycloalkoxy, halo $C_{1-6}$ alkyl, halo $C_{1-6}$ alkoxy, $C_{6-14}$ aryl, $C_{1-6}$ alkoxy-$C_{6-14}$ aryl, $C_{6-14}$ aryloxy, $C_{6-14}$ arylsulfonyl, nitro, $C_{1-6}$ alkoxycarbonyl, carboxyl, acetamide, hydroxyl, 5- to 14-membered aromatic heterocyclic groups, $CF_3$—, $CF_3O$—, Z—CO— {where Z represents —$NR^7R^8$ (wherein $R^7$ and $R^8$ may be the same or different and each represents hydrogen atom, $C_{1-6}$ alkyl, $C_{3-8}$ cycloalkyl, $C_{6-14}$ aryl, benzyl or $C_{3-8}$ cycloalkylmethyl), 1-pyrrolidinyl or 1-piperidyl}, amino $C_{1-6}$ alkyl, $C_{1-6}$ alkylenedioxy and the like, among which there are preferred halogen atoms, $C_{1-6}$ alkyl, $C_{1-6}$ alkoxy, $C_{1-6}$ alkylsulfonyl, halo $C_{1-6}$ alkyl, halo $C_{1-6}$ alkoxy, $C_{6-14}$ arylsulfonyl, nitro, carboxyl, acetamide, Z—CO— (where Z represents —$NR^7R^8$ (wherein $R^7$ and $R^8$ may be the same or different and each represents hydrogen atom or $C_{1-6}$ alkyl)} and $C_{1-6}$ alkylenedioxy. These substituents may also be bonded together to form rings. The number of substituents need only be within the range of the number of substituent-bindable positions, with 1–3 being preferred.

The scope of "pharmacologically acceptable salt" according to the present specification is not particularly restricted, and for example, there may be mentioned salts of inorganic acids, salts of organic acids, salts of inorganic bases, salts of organic bases, salts of acidic or basic amino acids and the like. As preferred examples of salts of inorganic acids there may be mentioned salts of hydrochloric acid, hydrobromic acid, sulfuric acid, nitric acid, phosphoric acid and the like, and as preferred examples of salts of organic acids there may be mentioned salts of acetic acid, succinic acid, fumaric acid, maleic acid, tartaric acid, citric acid, lactic acid, stearic acid, benzoic acid, methanesulfonic acid, p-toluenesulfonic acid and the like. As preferred examples of salts of inorganic bases there may be mentioned alkali metal salts such as sodium salts, potassium salts and the like, alkaline earth metal salts such as calcium salts, magnesium salts and the like, and aluminum salts, ammonium salts, or the like. As preferred examples of salts of organic bases there may be mentioned salts of diethylamine, diethanolamine, meglumine, N,N'-dibenzylethylenediamine and the like. As preferred examples of salts of acidic amino acids there may be mentioned salts of aspartic acid, glutamic acid and the like, and as preferred examples of salts of basic amino acids there may be mentioned salts of arginine, lysine, ornithine and the like.

The aforementioned acids or bases are those that form salts at an appropriate ratio in a range of 0.1–5 molecules per molecule of the compound. The pharmacologically acceptable salts of the amidino derivatives of the invention also include prodrugs, and for example, the aforementioned amidino derivative esters may be mentioned, with t-butyl esters being preferred.

The amidino derivatives of the invention or their pharmacologically acceptable salts may be in the form of solvates, where such solvates are preferably hydrates.

A process for production of the amidino derivatives and their pharmacologically acceptable salts or solvates according to the invention will now be explained. The amidino derivatives of the invention are novel compounds which may be synthesized in the following manner, as an example.

Specifically, the amidino derivatives of the invention represented by general formula (I) above may be synthesized utilizing ordinary organic chemical reactions which are already known, and for example, they may be synthesized by the process represented by the reaction scheme (A) shown below, or by a similar process. The symbols of the compounds in the following schemes are the same as defined above.

Production Scheme A

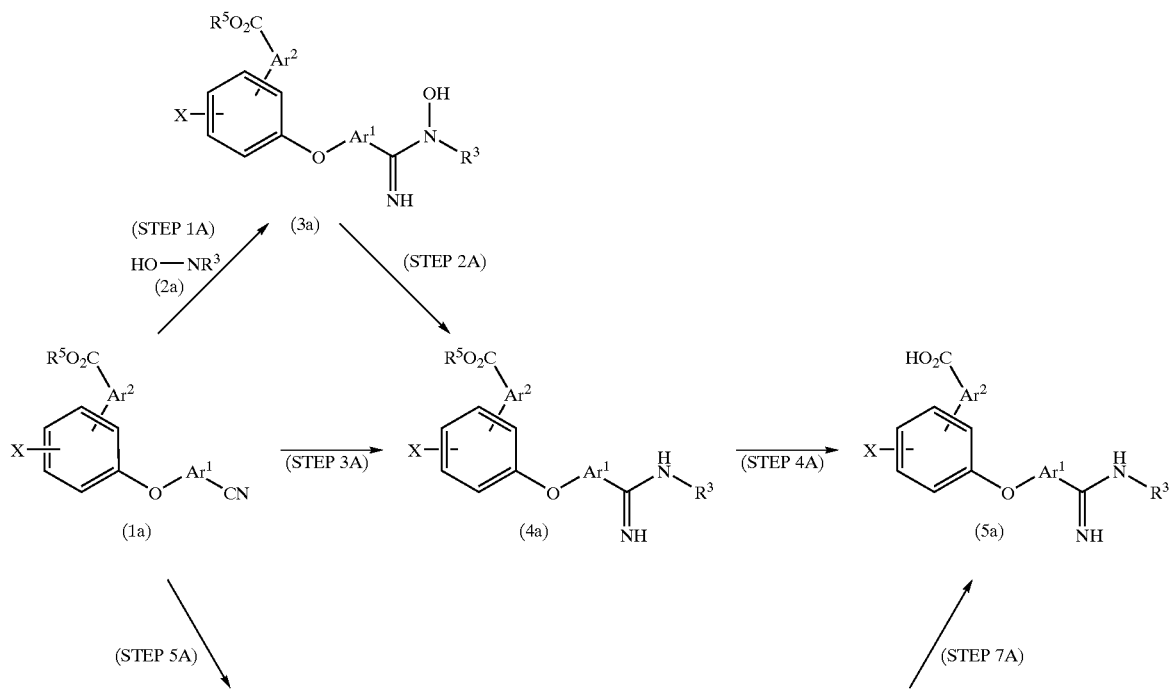

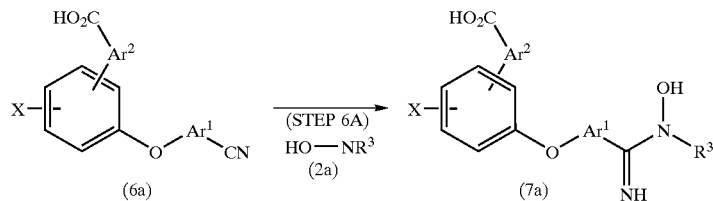

[Step 1A]

Compound (1a) may be reacted by the same procedure described in Synthetic Communications, Vol. 26 (23), p. 4351, 1996 to obtain compound (3a). Specifically, compound (1a) and a hydroxyamine (2a) are reacted in a solvent (for example, methanol or ethanol) in the presence of a base (for example, potassium carbonate).

[Step 2A]

Compound (3a) may be reacted by the same procedure described in Synthetic Communications, Vol. 26 (23), p. 4351, 1996 to obtain compound (4a). Specifically, compound (3a) and acetic anhydride are reacted in a solvent (for example, acetic acid), and then a palladium catalyst is added for reaction in hydrogen gas.

[Step 3A]

Compound (4a) can also be produced by employing the Pinner method. In the publicly known Pinner method, reaction is first conducted from −10° C. to 50° C. using hydrochloric acid in a solvent (for example, methanol, ethanol or methylene chloride), and then reaction is conducted from −10° C. to 50° C. using ammonia gas in a solvent (for example, methanol or ethanol).

[Step 4A]

Compound (4a) may be hydrolyzed in an acid (for example, hydrochloric acid, trifluoroacetic acid or sulfuric acid) to obtain compound (5a). Specifically, compound (4a) is reacted in a solvent (for example, tetrahydrofuran) in the presence of the aforementioned acid.

[Step 5A]

Compound (1a) may be hydrolyzed in an aqueous solution of a base (for example, sodium hydroxide or lithium hydroxide) to obtain compound (6a). Specifically, compound (1a) is reacted in a solvent (for example, a mixture of tetrahydrofuran and methanol) in the presence of the aforementioned base aqueous solution.

[Step 6A]

Compound (6a) and compound (2a) may be used to obtain compound (7a) by the same method as Step 1A.

[Step 7A]

Compound (7a) may be used to obtain compound (5a) by the same method as Step 2A.

In order to efficiently obtain each compound, the synthesis may be carried out using combinatorial chemistry. That is, a library for compound (5a) may be constructed by combination of substituent types and positions in compound (5a). Purification and identification of the bulk compounds are accomplished in a fully automatic manner by high-performance liquid chromatography (HPLC) and mass spectrometry (MS). Specifically, the compounds are purified by LC and simultaneously identified based on detection of $(M+1)^+$ by MS.

Compound (1a) used in the above scheme may be synthesized by Production Scheme B or Production Scheme C below.

Production Scheme B

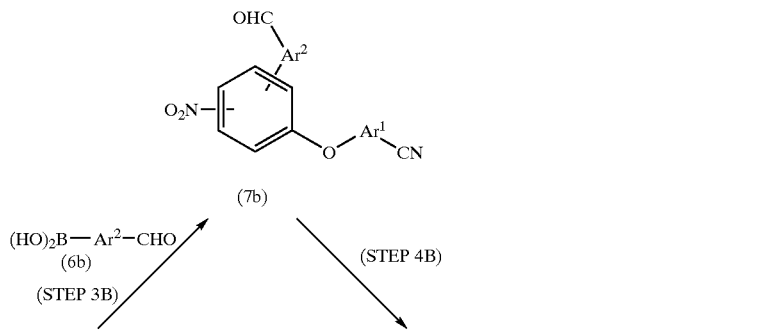

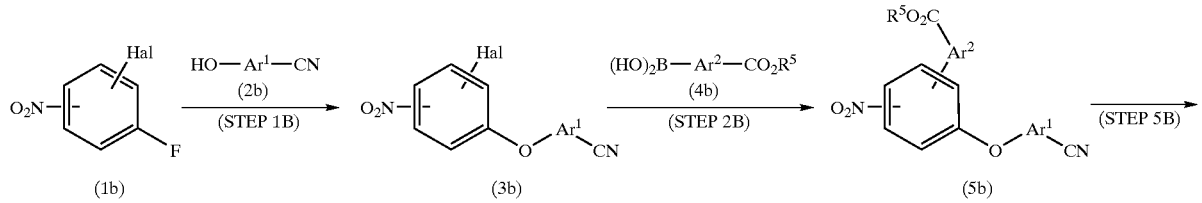

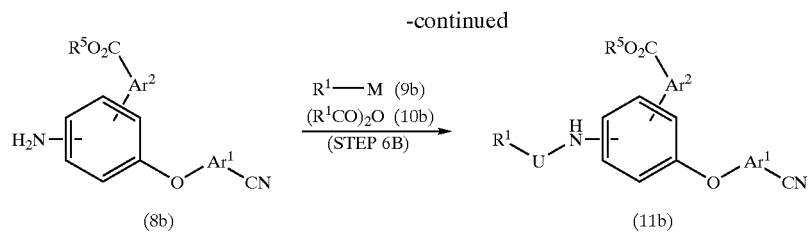

(In the above scheme, M represents a carboxylic acid group, an acid chloride group, a sulfonyl chloride group or an isocyanate group, and U represents —CO—, —SO$_2$— or —NHCO—.)

[Step 1B]

Compound (1b) and compound (2b) are reacted in a solvent (for example, THF, methylene chloride, acetonitrile or DMF) in the presence of a base to obtain compound (3b). As bases there may be mentioned basic salts such as sodium carbonate, potassium carbonate, cesium carbonate and the like, inorganic bases such as sodium hydroxide, potassium hydroxide, potassium fluoride and the like, aromatic amines such as pyridine, lutidine and the like, tertiary amines such as triethylamine, tripropylamine, tributylamine, cyclohexyldimethylamine, diisopropylethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, and metal alkoxides such as sodium methoxide, sodium ethoxide, potassium tert-butoxide and the like. The reaction may be conducted for 0.5 to 24 hours at a temperature from –80 to 150° C. and preferably –50 to 120° C. The product may be used either directly as the reaction solution or as a crude substance for the subsequent reaction, or it may be isolated from the reaction mixture according to ordinary methods, or easily purified by separating means such as recrystallization, distillation, chromatography or the like.

[Step 2B]

Compound (3b) and compound (4b) may be coupled according to the procedure described in Tetrahedron Lett., Vol. 33, p. 7433, 1992 to obtain compound (5b). Specifically, compound (3b) and compound (4b) are reacted in the presence of a palladium catalyst and base. The product may be used either directly as the reaction solution or as a crude substance for the subsequent reaction, or it may be isolated from the reaction mixture according to ordinary methods, or easily purified by separating means such as recrystallization, distillation or chromatography.

[Step 3B]

Compound (3b) and compound (6b) may be used to obtain compound (7b) by the same method as in Step 2B above.

[Step 4B]

Compound (7b) may be oxidized in a solvent (for example, acetonitrile or dichloromethane) in the presence of an oxidizing agent, scavenger and buffer to obtain a carboxylic acid. Sodium chlorite may be used as the oxidizing agent. As the scavenger there may be used 2-methyl-2-butene, sulfamic acid, or the like. The buffer may be sodium dihydrogen phosphate dihydrate. The obtained carboxylic acid may be, esterified according to the procedure described in T. W. Greene, Protective Groups in Organic Synthesis, Wiley, New York, 1991, to obtain compound (5b). For example, the compound may be reacted in a solvent (for example, toluene) in the presence of N,N-dimethylformamide and di-t-butyl acetal.

[Step 5B]

Compound (5b) may be reduced according to the same method described in Synlett, Vol. 9, p. 1028, 1998 to obtain compound (8b). Specifically, compound (5b) may be reacted in a solvent (for example, ethanol) in the presence of iron and ammonium chloride. Alternatively, it may be reacted in a solvent (for example, ethanol) in the presence of zinc and acetic acid to obtain compound (8b). The product may be used either directly as the reaction solution or as a crude substance for the subsequent reaction, or it may be isolated from the reaction mixture according to ordinary methods, or easily purified by separating means such as recrystallization, distillation, chromatography or the like.

[Step 6B]

Compound (8b) and R$^1$-M (9b) (where M represents COCl, SO$_2$Cl or NCO) or (R$^1$—CO)$_2$O (10b) may be reacted in a solvent (for example, tetrahydrofuran (hereinafter abbreviated as THF), methylene chloride, acetonitrile, dimethylformamide (hereinafter abbreviated as DMF) or toluene) in the presence of a base to obtain compound (11b). The use of a solvent in this case is optional. As bases there may be mentioned aromatic amines such as pyridine, lutidine and the like, and tertiary amines such as triethylamine, tripropylamine, tributylamine, cyclohexyldimethylamine, diisopropylethylamine, 4-dimethylaminopyridine, N,N-dimethylaniline, N-methylpiperidine, N-methylpyrrolidine and N-methylmorpholine. The reaction may be conducted for 0.5 to 24 hours, and preferably 1–12 hours, at a temperature from –40 to 80° C. and preferably –10 to 60° C. The product may be used either directly as the reaction solution or as a crude substance for the subsequent reaction, or it may be isolated from the reaction mixture according to ordinary methods, or easily purified by separating means such as recrystallization, distillation, chromatography or the like.

Alternatively, compound (8b) and R$^1$-M (9b) (where M represents COOH) may be reacted in a solvent (for example, DMF, THF, toluene or methylene chloride) in the presence of a condensing agent and a base to obtain compound (11b). As condensing agents there may be mentioned 1,3-dicyclohexyl carbodiimide (DCC), 1-ethyl-3-[3-(dimethylamino)propyl]carbodiimide (EDC), tetramethylfluoroformamidium hexafluorophosphate (TFFH), O-(7-azabenzotriazol-1-yl)-1,1,3,3-tetramethyluronium hexafluorophosphate (HATU) and the like. As bases there may be mentioned aromatic amines such as pyridine, lutidine and the like, and tertiary amines such as triethylamine, tripropylamine, tributylamine, cyclohexyldimethylamine, diisopropylethylamine, 4-dimethylaminopyridine, N,N-dimethylaniline, N-methylpiperidine, N-methylpyrrolidine, N-methylmorpholine and the like. The reaction may be conducted for 0.5 to 24 hours, and preferably 1–12 hours, at a temperature from –40 to 80° C. and preferably –10 to 60°

C. The product may be used either directly as the reaction solution or as a crude substance for the subsequent reaction, or it may be isolated from the reaction mixture according to ordinary methods, or easily purified by separating means such as recrystallization, distillation, chromatography or the like.

suitable solvent. Purification and identification of the various compounds in each of the steps may be accomplished in a fully automatic manner by HPLC and MS, where purification by HPLC is conducted simultaneously with identification of the compounds based on detection of $(M+1)^+$ by MS.

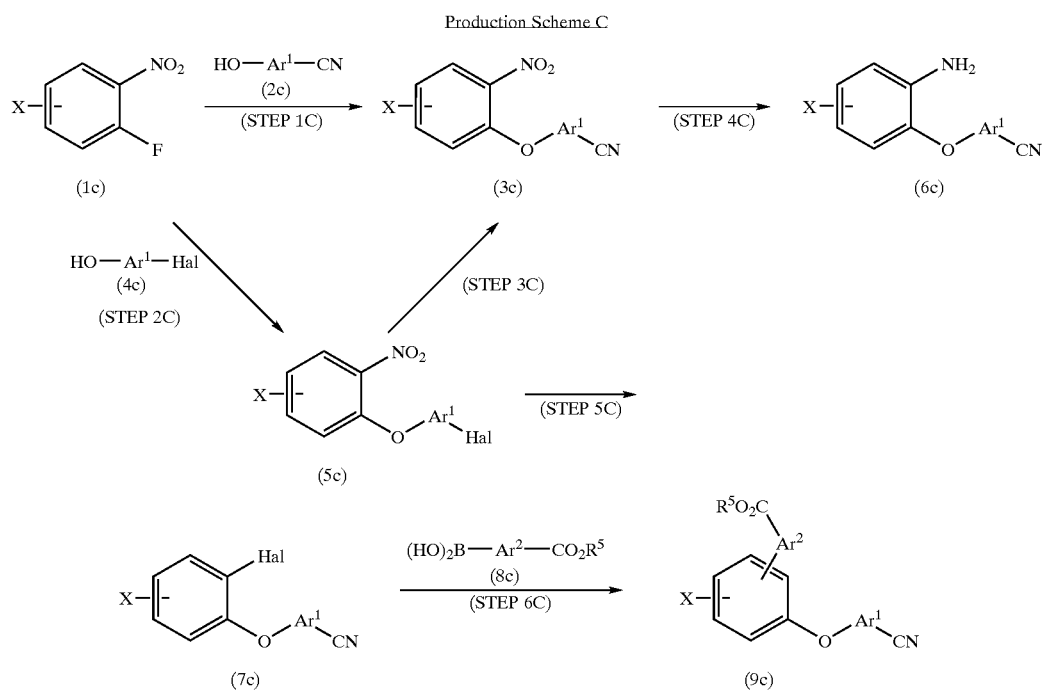

Production Scheme C

[Step 1C]
Compound (1c) and compound (2c) may be used to obtain compound (3c) by the same method as Step 1B above.

[Step 2C]
Compound (1c) and compound (4c) may be used to obtain compound (5c) by the same method as Step 1B above.

[Step 3C]
The halogen atom (Hal) of compound (5c) may be converted to a cyano group by the same method described in Synthetic Communications, Vol. 24, p. 889, 1994, to obtain compound (3c). Specifically, compound (5c) may be reacted in a solvent (for example, DMF) in the presence of zinc cyanide and a palladium catalyst.

[Step 4C]
Compound (3c) may be used to obtain compound (6c) by the same method as Step 5B above.

[Step 5C]
Compound (7c) may be obtained from compound (6c) using the Sandmeyer method described in Synthetic Communications, Vol. 22, (21), p. 3067, 1992. Specifically, compound (6c) and a nitrous acid ester may be reacted in the presence of a copper halide. The product may be used as a crude substance for the subsequent reaction, or it may be isolated from the reaction mixture according to ordinary methods, or easily purified by separating means such as recrystallization, distillation, chromatography or the like.

[Step 6C]
Compound (7c) and compound (8c) may be used to obtain compound (9c) by the same method as Step 2B above.

After completion of the reaction, the reaction product may be purified by any desired ordinary treatment method, for example, by column chromatography using silica gel, an adsorbing resin or the like, or recrystallization from a An amidino derivative of the invention, its pharmacologically acceptable salt or its solvate which is obtained in this manner may be used as a compound library. Further a set of 1 to 1 million amidino derivatives or their pharmacologically acceptable salts or their solvates may be used as a compound library.

Blood clotting factor VIIa inhibitors, anticoagulants and thrombosis therapeutic agents according to the invention will now be explained. The amidino derivatives of the invention and their pharmacologically acceptable salts and solvates inherently have serine protease inhibiting activity, and exhibit excellent inhibiting activity particularly against blood clotting factor VIIa. The amidino derivatives of the invention and their pharmacologically acceptable salts and solvates therefore function as blood clotting factor VIIa inhibitors (blood clotting factor VIIa enzyme activity inhibitors), and are hence useful as prophylactic and/or therapeutic agents for clinical conditions involving thrombogenesis in which extrinsic blood clotting mechanisms are implicated, i.e. as anticoagulants (particularly anticoagulants with inhibiting activity against blood clotting factor VIIa) or as thrombosis therapeutic agents.

As illnesses that may be prevented and/or treated by formulations according to the invention there may be mentioned thrombosis, deep venous thrombosis, pulmonary embolism, acute myocardial infarction, unstable angina, cerebral thrombosis, restenosis, arteriosclerosis and glomerulosclerosis.

The blood clotting factor VIIa inhibitors of the invention comprise the aforementioned amidino derivatives of the invention or their pharmacologically acceptable salts or solvates. The anticoagulants of the invention contain the aforementioned amidino derivatives of the invention or their pharmacologically acceptable salts or solvates as active ingredients. The thrombosis therapeutic agents of the invention also contain the aforementioned amidino derivatives of the invention or their pharmacologically acceptable salts or solvates as active ingredients.

The anticoagulants and thrombosis therapeutic agents of the invention may be formulated using ordinary formulation techniques, for use in the form of solid, semi-solid or liquid pharmaceutical formulations. Specifically, the active ingredient (an amidino derivative of the invention or its pharmacologically acceptable salt or solvate) may be combined with ordinary medicinally acceptable atoxic carriers to prepare any desired dosage form such as tablets, pellets, lozenges, capsules, granules, syrup, powder, suppository, cream, ointment, injection or the like. If necessary, adjuvants, stabilizers, thickeners, preservatives, osmotic regulating salts, buffering agents, coloring agents, aromas or the like may also be added to the formulation.

The content of the active ingredient in an anticoagulant or thrombosis therapeutic agent according to the invention is not particularly restricted, and may be appropriately selected depending on the dosage form. Also, two or more different active ingredients may be used in combination in an anticoagulant or thrombosis therapeutic agent of the invention.

A blood clotting factor VIIa inhibitor, anticoagulant or thrombosis therapeutic agent of the invention may be orally, enterally or intravenously administered, depending on the dosage form. The administered dose will differ considerably depending on the type of illness, severity of symptoms, patient age and gender, sensitivity to the drug agent and the like, but the daily dose for adults will generally be between about 0.03 mg and about 1000 mg, preferably between about 0.1 mg and about 500 mg and even more preferably between about 0.1 mg and about 100 mg. The dose may be administered at once or in divided doses per day, or at once or in divided doses every several days. In the case of injection, the dose will usually be from about 1 µg to about 3000 µg and preferably from about 3 µg to about 1000 µg per kg of body weight.

EXAMPLES

The present invention will now be explained in more specific detail through Production Examples and Examples, with the understanding that the invention is in no way limited to these examples. The symbol "↑" in the tables which follow indicates that the group is the same group as in the previous compound.

Production Example 1 t-Butyl 2-fluoro-5-nitrobenzoate

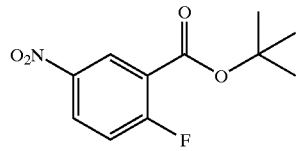

After dissolving 2-fluoro-5-nitrobenzoic acid (2.42 g) in toluene (30 ml), 1,1-di-tert-butoxytrimethylamine (10.6 g) was added dropwise over a period of 20 minutes while heating to reflux, and then the mixture was heated to reflux for another 30 minutes. After cooling to room temperature, washing was performed with saturated sodium bicarbonate solution and saturated saline, drying was performed over magnesium sulfate, and the solvent was distilled off. The residue was purified by silica gel chromatography (300 g, hexane:ethyl acetate=5:1) to obtain 2.48 g of t-butyl 2-fluoro-5-nitrobenzoate.

$^1$H-NMR (CDCl$_3$) δ: 1.61 (9H, s), 7.34 (1H, dd, J=8.8, 46.4 Hz), 8.23–8.28 (1H, m), 8.65 (1H, dd, J=2.4, 7.2 Hz).

Production Example 2-1 t-Butyl 2-(6-cyano-2-naphthyloxy)-5-nitrobenzoate

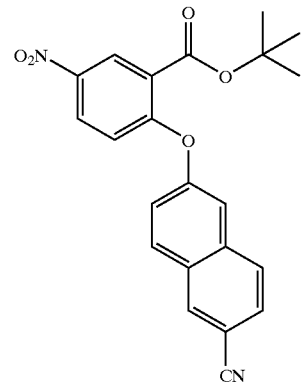

The compound (t-butyl 2-fluoro-5-nitrobenzoate) (1.74 g) obtained in a previous production example, 6-cyano-2-naphthol (1.86 g) and potassium carbonate (8.2 g) were heated to 50° C. in N,N-dimethylformamide and reacted for 2 hours. After cooling to room temperature, water was added and extraction was performed with ethyl acetate. The ethyl acetate layer was washed with saturated saline and dried over magnesium sulfate, and the solvent was distilled off. The residue was purified by silica gel chromatography (300 g, hexane:ethyl acetate=5:1) to obtain 3.23 g of t-butyl 2-(6-cyano-2-naphthyloxy)-5-nitrobenzoate.

$^1$H-NMR (CDCl$_3$) δ: 1.38 (9H, s), 7.05 (1H, d, J=9.2 Hz), 7.24 (1H, d, J=2.4 Hz), 7.32 (1H, dd, J=2.4, 8.8 Hz), 7.55 (1H, dd J=1.6, 8.4 Hz), 7.72 (1H, d, J=8.4 Hz), 7.89 (1H, d, J=8.8 Hz), 8.16 (1H, s), 8.25 (1H, dd, J=2.8, 8.8 Hz).

Production Examples 2-2 to 2-7

Compounds represented by the following formula (Ia):

HO—Ar—CN (where each Ar is the respective Ar in Table 1) were used to obtain compounds for Production Examples 2-2 to 2-7 by the same reaction as in Production Example 2-1.

TABLE 1

| PRODUCTION EXAMPLE | Ar | Y |
|---|---|---|
| 2-2 | 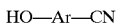 | COOtBu |

TABLE 1-continued

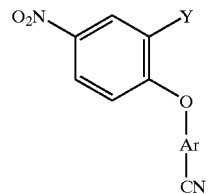

| PRODUCTION EXAMPLE | Ar | Y |
|---|---|---|
| 2-3 | 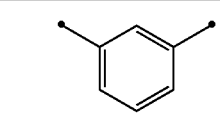 | ↑ |
| 2-4 | 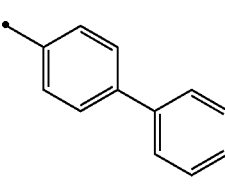 | ↑ |
| 2-5 | 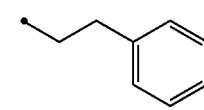 | ↑ |
| 2-6 | 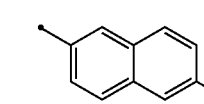 | Br |
| 2-7 | 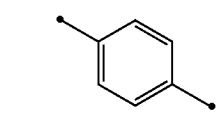 | ↑ |

Production Example 2-2 t-Butyl 2-(4-cyanophenoxy)-5-nitrobenzoate $^{1}$H-NMR (CDCl$_3$) δ: 1.44 (9H, s), 7.04 (2H, dd, J=2.0, 6.8 Hz), 7.15 (1H, d, J=8.8 Hz), 7.67 (2H, dd, J=2.0, 6.8 Hz), 8.35 (1H, dd, J=2.8, 9.2 Hz), 8.74 (1H, d, J=2.4).

Production Example 2-3 t-Butyl 2-(3-cyanophenoxy)-5-nitrobenzoate $^{1}$H-NMR (CDCl$_3$) δ: 1.48 (9H, s), 7.05 (1H, d, J=9.2 Hz), 7.24–7.28 (2H, m), 7.47–7.53 (2H, m), 8.33 (1H, dd, J=2.8, 9.2 Hz), 8.73 (1H, d, J=2.8 Hz).

Production Example 2-4 t-Butyl 2-(4-cyano-1,1'-biphenyl-4'-yloxy)-5-nitrobenzoate $^{1}$H-NMR (CDCl$_3$) δ: 1.53 (9H, s), 7.05 (1H, d, J=9.2 Hz), 7.15 (2H, dd, J=2.0, 6.8 Hz), 7.62–7.75 (6H, m), 8.27 (1H, dd, J=3.2, 9.2 Hz), 8.70 (1H, d, J=2.8 Hz).

Production Example 2-5 t-Butyl 2-[2-(4-cyanophenyl)ethoxy]-5-nitrobenzoate $^{1}$H-NMR (CDCl$_3$) δ: 1.59 (9H, s), 3.25 (2H, t, J=6.8 Hz), 4.33 (2H, t, J=6.0 Hz), 6.97 (1H, d, J=9.2 Hz), 7.47 (2H, d, J=8.8 Hz), 7.61 (2H, dd, J=1.6, 6.4 Hz), 8.28 (1H, dd, J=2.8, 9.2 Hz), 8.54 (1H, d, J=2.4 Hz).

Production Example 2-6

3-bromo-4-(6-cyano-2-naphthyloxy)nitrobenzene $^{1}$H-NMR (CDCl$_3$) δ: 7.02 (1H, d, J=9.2 Hz), 7.39 (1H, dd, J=2.4, 9.2 Hz), 7.41 (1H, s), 7.65 (1H, dd, J=2.0, 8.8 Hz), 7.83 (1H, d, J=8.4 Hz), 7.99 (1H, d, J=8.4 Hz), 8.17 (1H, dd, J=2.8, 9.2 Hz), 8.26 (1H, s), 8.61 (1H, d, 2.4 Hz).

Production Example 2-7

3-bromo-2-(4-cyanophenoxy)nitrobenzene $^{1}$H-NMR (CDCl$_3$) δ: 7.06–7.10 (3H, m), 7.71 (2H, dd, J=2.0, 6.8 Hz), 8.20 (1H dd, J=3.2, 9.6 Hz), 8.59 (1H, d, J=2.8 Hz).

Production Example 3-1

4-(6-cyano-2-naphthyloxy)-3-(2-formylphenyl)nitrobenzene

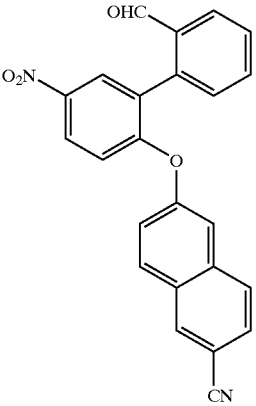

The compound (3-bromo-4-(6-cyano-2-naphthyloxy)nitrobenzene) (1 g) obtained in a previous production example, 2-formylphenyl boronic acid (610 mg) and tetrakis(triphenylphosphine)palladium (0) (150 mg) were heated to reflux and reacted for 6 hours in a mixture of 2 M sodium carbonate aqueous solution (10 ml), toluene (10 ml) and ethanol (10 ml). After cooling to room temperature, water was added and extraction was performed with ethyl acetate. The ethyl acetate layer was washed with saturated saline and dried over magnesium sulfate, and the solvent was distilled off. The residue was purified by silica gel chromatography (200 g, hexane:ethyl acetate=4:1) to obtain 880 mg of 4-(6-cyano-2-naphthyloxy)-3-(2-formylphenyl)nitrobenzene.

$^{1}$H-NMR (CDCl$_3$) δ: 7.02 (1H, d, J=9.2 Hz), 7.24 (1H, dd, J=2.4, 9.2 Hz), 7.35 (1H, d, J=2.4 Hz), 7.43 (1H, d, J=7.6 Hz), 7.56–7.63 (2H, m), 7.68 (1H, t, J=7.6 Hz), 7.78 (1H, d, J=8.8 Hz), 7.87 (1H, d, J=9.2 Hz), 7.96 (1H, d, J=7.6 Hz), 8.19 (1H, s) 8.27 (1H, dd, J=2.8, 8.8 Hz), 8.34 (1H, d, J=2.8 Hz), 10.04 (1H, s).

Production Examples 3-2 to 3-8

Compounds represented by the following formula (IIa):

$$(HO)_2B\text{—}Ar^2\text{—}CHO$$

(where each Ar$^2$ is the respective Ar$^2$ in Table 2) were used to obtain compounds for Production Examples 3-2 to 3-8 by the same reaction as in Production Example 3-1.

TABLE 2

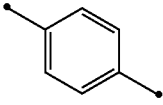

| PRODUCTION EXAMPLE | r | Ar² |
|---|---|---|
| 3-2 | 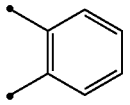 | 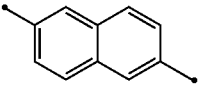 |
| 3-3 | 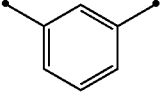 | 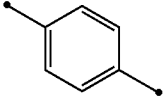 |
| 3-4 | 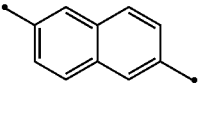 | ↑ |
| 3-5 | 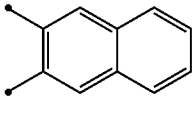 | 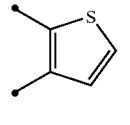 |
| 3-6 | ↑ | 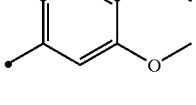 |
| 3-7 | ↑ | 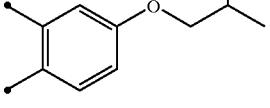 |
| 3-8 | ↑ | ↑ |

Production Example 3-2

2-(4-cyanophenoxy)-3-(2-formylphenyl)nitrobenzene

¹H-NMR (CDCl₃) δ: 6.97 (1H, d, J=9.2 Hz), 7.07 (1H, dd, J=0.8, 8.4 Hz), 7.36 (1H, dd, J=1.2, 7.6 Hz), 7.56–7.60 (3H, m), 7.65–7.69 (1H, m), 7.94 (1H, dd, J=1.6, 7.6 Hz), 8.28–8.32 (2H, m), 9.96 (1H, s).

Production Example 3-3

4-(6-cyano-2-naphthyloxy)-3-(3-formylphenyl)nitrobenzene

¹H-NMR (CDCl₃) δ: 7.26 (1H, d, J=8.8 Hz), 7.53 (1H, dd, J=2.4, 9.2 Hz), 7.67 (1H, t, J=7.6 Hz), 7.70 (1H, d, J=2.4 Hz), 7.77 (1H, dd, J=2.0, 8.8 Hz), 7.91 (1H, dd, J=1.2, 7.6 Hz), 8.00 (1H, s), 8.02 (1H, s), 8.13 (1H, d, J=8.8 Hz), 8.18 (1H, s), 8.28 (1H, dd, J=2.8, 8.8 Hz), 8.41 (1H, d J=2.8 Hz), 8.58 (1H, s), 10.04 (1H, s).

Production Example 3-4

2-(4-cyanophenoxy)-3-(3-formylphenyl)nitrobenzene

¹H-NMR (CDCl₃) δ: 7.02 (2H, dd, J=2.0, 6.8 Hz), 7.15 (1H, d, J=8.8 Hz), 7.59–7.63 (3H, m), 7.77–7.80 (3H, m), 7.89–7.91 (1H, m), 8.05–8.06 (1H, m), 8.27 (1H, dd, J=2.8, 9.2 Hz), 8.42 (1H, d, J=2.8 Hz), 10.05 (1H, s).

Production Example 3-5

4-(6-cyano-2-naphthyloxy)-3-(3-formyl-2-naphthyl)nitrobenzene

¹H-NMR (CDCl₃) δ: 7.17 (1H, d, J=9.2 Hz), 7.35 (1H, dd, J=2.0, 8.8 Hz), 7.61 (1H, d, J=2.0 Hz), 7.65–7.76 (3H, m), 7.98 (1H, d, J=8.8 Hz), 8.04–8.09 (3H, m), 8.17 (1H, d, J=8.4 Hz), 8.32 (1H, dd, J=2.8, 9.2 Hz), 8.40 (1H, d, J=2.8 Hz), 8.53 (1H, s), 8.59 (1H, s), 10.12 (1H, s).

Production Example 3-6

4-(6-cyano-2-naphthyloxy)-3-(2-formylthiophen-3-yl)nitrobenzene

¹H-NMR (CDCl₃) δ: 7.28 (1H, d, J=8.8 Hz), 7.45 (1H, d, J=4.8 Hz), 7.47 (1H, dd, J=2.4, 8.8 Hz), 7.68 (1H, d, J=2.4 Hz), 7.77 (1H, dd, J=1.6, 8.8 Hz), 7.99 (1H, d, J=8.8 Hz), 8.10–8.13 (2H, m), 8.33 (1H, dd, J=2.8, 9.2 Hz), 8.45 (1H, d, J=3.2 Hz), 8.57 (1H, s), 9.85 (1H, s).

Production Example 3-7

4-(6-cyano-2-naphthyloxy)-3-(4,5-dimethoxy-2-formylphenyl)nitrobenzene

¹H-NMR (CDCl₃) δ: 3.93 (3H, s), 3.96 (3H, s), 6.82 (1H, s), 7.06 (1H, d, J=9.2 Hz), 7.23 (1H, dd, J=2.4, 9.2 Hz), 7.35 (1H, d, J=2.4 Hz), 7.47 (1H, s), 7.62 (1H, dd, J=1.6, 8.8 Hz), 7.78 (1H, d, J=8.4 Hz), 7.88 (1H, d, J=8.8 Hz), 8.20 (1H, s), 8.27 (1H, dd, J=2.8, 9.2 Hz), 8.36 (1H, d, J=2.8 Hz), 9.87 (1H, s).

Production Example 3-8

4-(6-cyano-2-naphthyloxy)-3-(2-formyl-4-[2-methylpropoxy]phenyl)nitrobenzene

¹H-NMR (CDCl₃) δ: 1.03 (6H, d, J=6.8 Hz), 2.08 (1H, m), 3.79 (2H, d, J=6.8 Hz), 7.03 (1H, d, J=9.2 Hz), 7.18–7.24 (2H, m), 7.32 (1H, s), 7.34 (1H, d, J=6.0 Hz), 7.45 (1H, d, J=2.8 Hz), 7.61 (1H, d, J=1.6, 8.8 Hz), 7.77 (1H, d, J=8.8 Hz), 7.88 (1H, d, J=9.2 Hz), 8.19 (1H, s), 8.25 (1H, dd, J=3.2, 9.2 Hz), 8.33 (1H, d, J=2.8 Hz), 9.97 (1H, s).

Production Example 3-9

Methyl 2'-(6-cyano-2-naphthyloxy)-4-[(2-methylpropyl)carbamoyl]-5'-nitro-1,1'-biphenyl-2-carboxylate

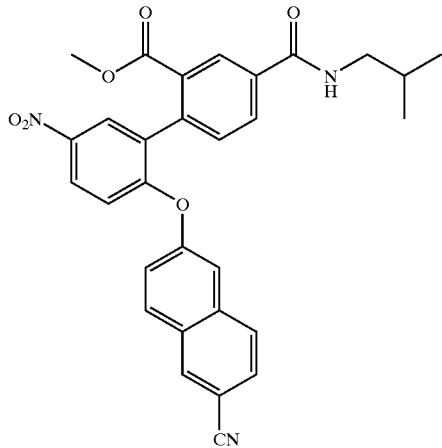

The title compound was obtained by the same process as in Production Example 3-1, except that pinacol 4-[(2-methylpropyl)carbamoyl-3-methoxycarbonylphenylborohate was used instead of 2-formylphenylboronic acid.

$^1$H-NMR (CDCl$_3$) δ: 0.99 (6H, d, J=6.8 Hz), 1.87–1.95 (1H, m), 3.31 (2H, dd, J=6.8, 6.0 Hz), 3.74 (3H, s), 6.21 (1H, brs), 7.01 (1H, d, J=9.2 Hz), 7.25–7.29 (1H, m), 7.36 (1H, d, J=2.4 Hz), 7.49 (1H, d, J=8.4 Hz), 7.60 (1H, dd, J=1.8, 8.6 Hz), 7.77 (1H, d, J=8.8 Hz), 7.88 (1H, d, J=9.2 Hz), 8.02 (1H, dd, J=2.0, 8.0 Hz), 8.20 (1H, s), 8.24 (1H, dd, J=2.8, 9.2 Hz), 8.29 (1H, d, J=2.4 Hz), 8.34 (1H, d, J=2.0 Hz).

Production Example 4-1 t-Butyl 2'-(6-cyano-2-naphthyloxy)-5'-nitro-1,1'-biphenyl-2-carboxylate

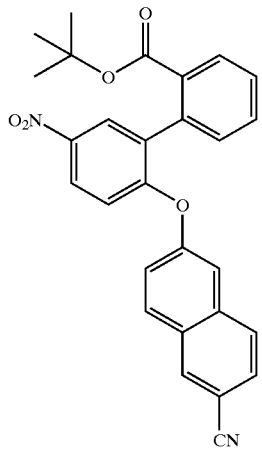

The compound (4-(6-cyano-2-naphthyloxy)-3-(2-formylphenyl)nitrobenzene) (800 mg) obtained in a previous production example, 2-methyl-2-butene (1.4 ml) and sodium dihydrogen phosphate dihydrate (2 g) were dissolved in acetonitrile:water (2:1, 50 ml) and then sodium chlorate (1 g) was added. After reaction for one hour at room temperature, 1 N hydrochloric acid water was added and extraction was performed with ethyl acetate. The ethyl acetate layer was washed with 1N hydrochloric acid water and saturated saline and then dried over magnesium sulfate, and the solvent was distilled off to obtain 5'-nitro-2'-(6-cyano-2-naphthyloxy)-1,1'-biphenyl-2-carboxylic acid (800 mg). This was dissolved in toluene without purification and subjected to the same process as in Production Example 1 to obtain t-butyl 2'-(6-cyano-2-naphthyloxy)-5'-nitro-1,1'-biphenyl-2-carboxylate.

$^1$H-NMR (CDCl$_3$) δ: 1.38 (9H, s), 7.08 (1H, dd, J=0.8, 9.2 Hz), 7.25 (1H, dd, J=2.4, 8.4 Hz), 7.29–7.33 (2H, m), 7.41 (1H, t, J=7.6 Hz), 7.49 (1H, t, J=7.6 Hz), 7.57 (1H, d, J=7.6 Hz), 7.72 (1H, d, J=8.4 Hz), 7.81 (1H, d, J=8.8 Hz), 7.93 (1H, d, J=7.6 Hz), 8.15 (1H, s), 8.24 (1H, ddd, J=0.8, 2.8, 8.8 Hz), 8.29 (1H, dd, J=0.8, 2.8 Hz).

Production Examples 4-2 to 4-8

The compounds {2-(4-cyanophenoxy)-3-(2-formylphenyl)nitrobenzene, 4-(6-cyano-2-naphthyloxy)-3-(3-formylphenyl)nitrobenzene, 2-(4-cyanophenoxy)-3-(3-formylphenyl)nitrobenzene, 4-(6-cyano-2-naphthyloxy)-3-(3-formyl-2-naphthyl)nitrobenzene, 4-(6-cyano-2-naphthyloxy)-3-(2-formylthiophen-3-yl)nitrobenzene, 4-(6-cyano-2-naphthyloxy)-3-(4,5-dimethoxy-2-formylphenyl)nitrobenzene and 4-(6-cyano-2-naphthyloxy)-3-(2-formyl-4-[2-methylpropoxy]phenyl)nitrobenzene} obtained in previous production examples, were used for the same reaction as in Production Example 4-1 to obtain compounds for Production Examples 4-2 to 4-8, respectively.

TABLE 3

| PRODUCTION EXAMPLE | Ar | Ar² |
|---|---|---|
| 4-2 | *para-phenylene* | *ortho-phenylene* |
| 4-3 | 2,6-naphthylene | *meta-phenylene* |
| 4-4 | *para-phenylene* | ↑ |
| 4-5 | 2,6-naphthylene | 2,3-naphthylene |

TABLE 3-continued

O₂N—Ar²(—COOtBu)—O—Ar—CN

| PRODUC-TION EXAMPLE | Ar | Ar² |
|---|---|---|
| 4-6 | ↑ | (thiophene) |
| 4-7 | ↑ | (4,5-dimethoxyphenyl) |
| 4-8 | ↑ | (2-methylpropoxy-phenyl) |

Production Example 4-2 t-Butyl 2'-(4-cyanophenoxy)-5'-nitro-1,1'-biphenyl-2-carboxylate $^1$H-NMR (CDCl$_3$) δ: 1.30 (9H, s), 6.87 (1H, d, J=8.8 Hz), 7.05 (1H dd, J=0.8, 8.0 Hz), 7.17–7.20 (1H, m), 7.33–7.47 (3H, m), 7.85 (1H, dd, J=1.6, 7.6 Hz), 8.18–8.21 (2H, m).

Production Example 4-3 t-Butyl 2'-(6-cyano-2-naphthyloxy)-5'-nitro-1,1'-biphenyl-3-carboxylate $^1$H-NMR (CDCl$_3$) δ: 1.55 (9H, d), 7.12 (1H, d, J=8.8 Hz), 7.32 (1H, dd, J=2.4, 9.2 Hz), 7.36 (1H, d, J=2.4 Hz), 7.48 (1H, t, J=7.6 Hz ), 7.61 (1H, dd, J=1.6, 8.8 Hz), 7.73–7.79 (2H, m), 7.92 (1H, d, J=9.2 Hz), 7.98–8.01 (1H, m), 8.20–8.24 (3H, m), 8.43 (1H, d, J=2.8 Hz).

Production Example 4-4 t-Butyl 2'-(4-cyanophenoxy)-5'-nitro-1,1'-biphenyl-3-carboxylate $^1$H-NMR (CDCl$_3$) δ: 1.50 (9H, s), 6.93–6.97 (2H, m), 7.08 (1H, d, J=9.2 Hz), 7.38–7.42 (1H, m), 7.53–7.61 (3H, m), 7.92–7.94 (1H, m), 8.05–8.06 (1H, m), 8.17–8.20 (1H, m), 8.35 (1H, d, J=2.8 Hz).

Production Example 4-5 t-Butyl 3-[2-(6-cyano-2-naphthyloxy)-5-nitrophenyl]-naphthalene-2-carboxylate $^1$H-NMR (CDCl$_3$) δ: 1.43 (9H, s), 7.09 (1H, d, J=9.2 Hz), 7.24–7.27 (1H, m), 7.32 (1H, d, J=2.4 Hz), 7.53–7.60 (3H, m), 7.70 (1H, d, J=8.4 Hz), 7.79 (1H, d, J=8.8 Hz), 7.80 (1H, s), 7.84 (1H, d, J=7.6 Hz), 7.93 (1H, d, J=7.6 Hz), 8.12 (1H, s), 8.26 (1H, dd, J=12.8, 9.2 Hz), 8.43 (1H, d, J=2.4 Hz), 8.48 (1H, s).

Production Example 4-6 t-Butyl 3-[2-(6-cyano-2-naphthyloxy)-5-nitrophenyl]-thiophene-2-carboxylate $^1$H-NMR (CDCl$_3$) δ: 1.41 (9H, s), 7.04–7.07 (2H, m), 7.32 (1H, dd, J=2.4, 8.8 Hz), 7.37 (1H, d, J=2.0 Hz), 7.46 (1H, dd, J=0.8, 5.2 Hz ), 7.59 (1H, dd, J=0.8, 8.4 Hz), 7.75 (1H, d, J=8.4 Hz), 7.86 (1H, dd, J=8.8 Hz), 8.19 (1H, s), 8.20–8.23 (1H, m), 8.32 (1H, d, J=2.4 Hz).

Production Example 4-7 t-Butyl 2'-(6-cyano-2-naphthyloxy)-4,5-dimethoxy-5'-nitro-1,1'-biphenyl-2-carboxylate $^1$H-NMR (CDCl$_3$) δ: 1.34 (9H, s), 3.84 (3H, s), 3.91 (3H, s), 6.71 (1H, s), 7.08 (1H, d, J=8.8 Hz), 7.24 (1H, d, J=2.8 Hz), 7.30 (1H, d, J=2.8 Hz), 7.48 (1H, s), 7.58 (1H, dd, J=1.6, 8.4 Hz), 7.72 (1H, d, J=8.8 Hz), 7.82 (1H, d, J=8.8 Hz ), 8.17 (1H, s), 8.23 (1H, dd, J=2.8, 8.8 Hz), 8.27 (1H, d, J=3.2 Hz).

Production Example 4-8 t-Butyl 2'-(6-cyano-2-naphthyloxy)-4-(2-methylpropoxy)-5'-nitro-1,1'-biphenyl-2-carboxylate $^1$H-NMR (CDCl$_3$) δ: 1.01 (6H, d, J=6.8 Hz), 1.36 (9H, s), 2.06 (1H, m), 3.73 (2H, d, J=6.8 Hz), 6.99 (1H, dd, J=2.8, 8.8 Hz), 7.08 (1H, d, J=8.8 Hz), 7.20–7.27 (3H, m), 7.43 (1H, d, J=2.8 Hz), 7.57 (1H, dd, J=1.6, 8.8 Hz), 7.72 (1H, d, J=8.8 Hz), 7.81 (1H, d, J=9.2 Hz), 8.15 (1H, s), 8.21 (1H, dd, J=2.8, 8.8 Hz), 8.27 (1H, d, J=2.8 Hz).

Production Example 5-1 t-Butyl 5-amino-2-(6-cyano-2-naphthyloxy)benzoate

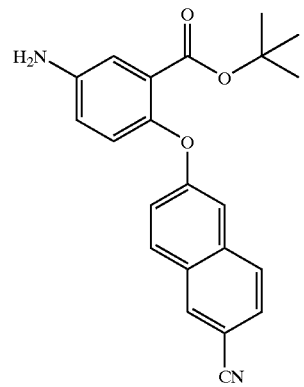

The compound (t-butyl 2-(6-cyano-2-naphthyloxy)-5-nitrobenzoate) (760 mg) obtained in a previous production example, iron powder (718 mg) and ammonium chloride (73 mg) were heated to reflux in ethanol:water (3:1, 30 ml) and reacted for 30 minutes. The insoluble portion was immediately filtered using celite, and the filtrate was concentrated. A saturated sodium bicarbonate solution was added to the obtained residue, and extraction was performed with ethyl acetate. The ethyl acetate layer was washed with saturated saline and then dried over magnesium sulfate, and the solvent was distilled off to obtain 736 mg of t-butyl 5-amino-2-(6-cyano-2-naphthyloxy)benzoate.

$^1$H-NMR (d$_6$-DMSO) δ: 1.12 (9H, s), 5.35 (1H, brd), 6.79 (1H, dd, J=2.4, 8.4 Hz), 6.92 (1H, d, J=8.8 Hz), 6.99 (1H, d, J=2.8 Hz), 7.01 (1H, d, J=2.8 Hz), 7.35 (1H, dd, J=2.4, 8.8 Hz), 7.64 (1H, dd, J=1.6, 8.8 Hz), 7.89 (1H, d, J=8.4 Hz), 8.01 (1H, d, J=9.2 Hz), 8.46 (1H, s).

Production Examples 5-2 to 5-13

The compounds {t-butyl 2-(6-cyano-2-naphthyloxy)-5-nitrobenzoate, t-butyl 2-(4-cyanophenoxy)-5-nitrobenzoate, t-butyl 2-(3-cyanophenoxy)-5-nitrobenzoate, t-butyl 2-(4-cyano-1,1'-biphenyl-4'-yloxy)-5-nitrobenzoate, t-butyl 2-[2-(4-cyanophenyl)ethoxy]-5-nitrobenzoate, t-butyl 2'-(6-cyano-2-naphthyloxy)-5'-nitro-1,1'-biphenyl-2-carboxylate, t-butyl 2'-(4-cyanophenoxy)-5'-nitro-1,1'-biphenyl-2-carboxylate, t-butyl 2'-(6-cyano-2-naphthyloxy)-5'-nitro-1,1'-biphenyl-3-carboxylate, t-butyl 2'-(4-cyanophenoxy)-5'-nitro-1,1'-biphenyl-3-carboxylate, t-butyl 3-[2-(6-cyano-2-naphthyloxy)-5-nitrophenyl]-naphthalene-2-carboxylate, t-butyl 3-[2-(6-cyano-2-naphthyloxy)-5-nitrophenyl]-thiophene-2-carboxylate, t-butyl 2'-(6-cyano-2-naphthyloxy)-4,5-dimethoxy-5'-nitro-1,1'-biphenyl-2-carboxylate, t-butyl 2'-(6-cyano-2-naphthyloxy)-4-(2-methylpropoxy)-5'-nitro-1,1'-biphenyl-2-carboxylate and methyl 2'-(6-cyano-2-naphthyloxy)-4-[(2-methylpropyl)carbamoyl]-5'-nitro-1,1'-biphenyl-2-carboxylate} obtained in the previous production examples, were used for the same reaction as in Production Example 5-1 to obtain compounds for Production Examples 5-2 to 5-13, respectively.

TABLE 4

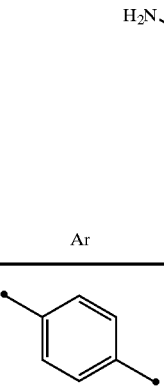

| Example | Ar | A |
|---|---|---|
| 5-2 | 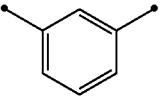 | COOtBu |
| 5-3 | 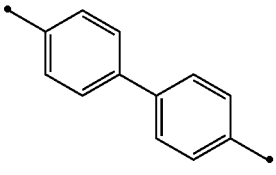 | ↑ |
| 5-4 | 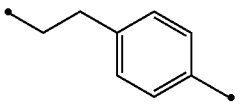 | ↑ |
| 5-5 | 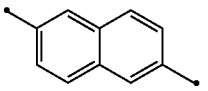 | ↑ |
| 5-6 | 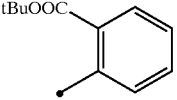 | 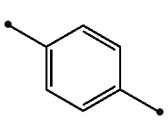 |
| 5-7 |  | ↑ |

TABLE 4-continued

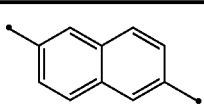

| Example | Ar | A |
|---|---|---|
| 5-8 | 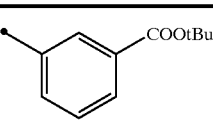 | 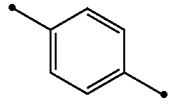 |
| 5-9 | 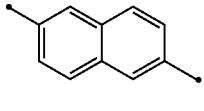 | ↑ |
| 5-10 | 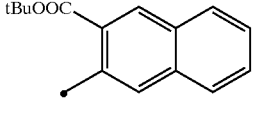 | 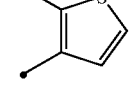 |
| 5-11 | ↑ | 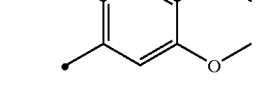 |
| 5-12 | ↑ | 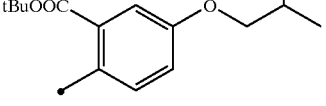 |
| 5-13 | ↑ | 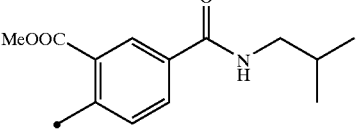 |
| 5-14 | ↑ | 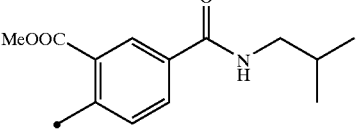 |

Production Example 5-2 t-Butyl 5-amino-2-(4-cyanophenoxy)benzoate $^1$H-NMR (d$_6$-DMSO) δ: 1.19 (9H, s), 5.38 (1H, brd), 6.77 (1H, dd, J=3.2, 8.8 Hz), 6.85–6.88 (3H, m), 6.97 (1H, d, J=2.8 Hz), 7.73 (2H, dd, J=2.0, 6.8 Hz).

Production Example 5-3 t-Butyl 5-amino-2-(3-cyanophenoxy)benzoate $^1$H-NMR (d$_6$-DMSO) δ: 1.20 (9H, s), 5.35 (1H, brd, J=7.6 Hz), 6.76 (1H, dd, J=3.2, 8.8 Hz), 6.68 (1H, d, J=8.8 Hz), 6.96 (1H, d, J=2.8 Hz), 7.05 (1H, m), 7.13 (1H, brs), 7.39–7.48 (2H, m).

Production Example 5-4 t-Butyl 5-amino-2-(4-cyano-1,1'-biphenyl-4'-yloxy)benzoate $^1$H-NMR (d$_6$-DMSO) δ: 1.23 (9H, s), 5.29 (1H, brd, J=7.6 Hz), 6.76 (1H, dd, J=2.8, 8.4 Hz), 6.82–6.87 (3H, m), 6.95 (1H, d, J=2.8 Hz), 7.68 (2H, dd, J=2.0, 6.8 Hz), 7.78–7.87 (4H, m).

Production Example 5-5 t-Butyl 5-amino-2-[2-(4-cyanophenyl)ethoxy]benzoate $^1$H-NMR (d$_6$-DMSO) δ: 1.42 (9H, s), 3.04 (2H, t, J=6.4 Hz), 4.07 (2H, t, J=6.8 Hz), 4.81 (1H, brd, J=8.8 Hz), 6.61

(1H, dd, J=2.4, 8.4 Hz), 6.71 (1H, d, J=3.2 Hz), 6.76 (1H, d, J=8.8 Hz), 7.50 (2H, d, J=8.0 Hz), 7.73 (2H, dd, J=2.0, 6.8 Hz).

Production Example 5-6 t-Butyl 5'-amino-2'-(6-cyano-2-naphthyloxy)-1,1'-biphenyl-2-carboxylate $^1$H-NMR (d$_6$-DMSO) δ: 1.32 (9H, s), 5.15 (1H, brd, J=8 Hz), 6.55 (1H, d, J=2.8 Hz), 6.64 (1H, dd, J=2.8, 8.8 Hz), 6.88 (1H, d, J=6 Hz), 7.01 (1H, d, J=2.4 Hz), 7.09 (1H, dd, J=2.4, 9.2 Hz), 7.19–7.23 (2H, m), 7.31 (1H, t, J=7.2 Hz), 7.56 (1H, d, J=7.6 Hz), 7.59 (1H, d, J=8.4 Hz), 7.78 (1H, d, J=8.8 Hz), 7.83 (1H, d, J=9.2 Hz), 8.35 (1H, s).

Production Example 5-7 t-Butyl 5'-amino-2'-(4-cyanophenoxy)-1,1'-biphenyl-2-carboxylate $^1$H-NMR (d$_6$-DMSO) δ: 1.30 (9H, s), 5.18 (1H, brs), 6.52 (1H, d, J=2.4 Hz), 6.61 (1H, dd, J=2.8, 8.8 Hz), 6.72–6.75 (2H, m), 6.83 (1H, d, J=8.4 Hz), 7.18 (1H, dd, J=0.8, 7.2 Hz), 7.25–7.29 (1H, m), 7.36–7.40 (1H, m), 7.54–7.59 (2H, m).

Production Example 5-8 t-Butyl 5'-amino-2'-(6-cyano-2-naphthyloxy)-1,1'-biphenyl-3-carboxylate $^1$H-NMR (d$_6$-DMSO) δ: 1.33 (9H, s), 5.26 (1H, brd, J=8.4 Hz), 6.68 (1H, dd, J=2.8, 8.8 Hz), 6.73 (1H, d, J=2.4 Hz), 6.96 (1H, d, J=8.8 Hz), 7.14 (1H, d, J=2.4 Hz), 7.27 (1H, dd, J=2.8, 9.2 Hz), 7.42 (1H, t, J=7.6 Hz), 7.62–7.65 (2H, m), 7.70–7.73 (1H, m), 7.87–7.91 (2H, m), 7.95 (1H, d, J=8.8 Hz), 8.44 (1H, s).

Production Example 5-9 t-Butyl 5'-amino-2'-(4-cyanophenoxy)-1,1'-biphenyl-3-carboxylate $^1$H-NMR (d$_6$-DMSO) δ: 1.45 (9H, s), 5.28 (1H, brd, J=8.0 Hz), 6.66 (1H, dd, J=2.8, 8.4 Hz), 6.70 (1H, d, J=2.4 Hz), 6.86–6.91 (3H, m), 7.44 (1H, t, J=7.6 Hz), 7.59–7.61 (1H, m), 7.68 (2H, d, J=8.8 Hz), 7.76 (1H, dd, J=1.2, 8.0 Hz), 7.82 (1H, s).

Production Example 5-10 t-Butyl 3-[5-amino-2-(6-cyano-2-naphthyloxy)phenyl]-naphthalene-2-carboxylate $^1$H-NMR (d$_6$-DMSO) δ: 1.38 (9H, s), 5.19 (1H, brd, J=8.8 Hz), 6.68 (1H, dd, J=2.4, 8.4 Hz), 6.73 (1H, d, J=2.8 Hz), 6.91 (1H, d, J=8.8 Hz), 7.01 (1H, d, J=2.0 Hz), 7.09 (1H, dd, J=2.4, 9.2 Hz), 7.43–7.50 (2H, m), 7.55 (1H, dd, J=1.2, 8.4 Hz), 7.74–7.81 (3H, m), 7.92 (1H, d, J=8.8 Hz), 8.21 (1H, s), 8.28 (1H, s).

Production Example 5-11 t-Butyl 3-[5-amino-2-(6-cyano-2-naphthyloxy)phenyl]-thiophene-2-carboxylate $^1$H-NMR (d$_6$-DMSO) δ: 1.34 (9H, s), 5.15 (1H, brd, J=8.4 Hz), 6.56 (1H, d, J=2.8 Hz), 6.64 (1H, dd, J=2.8, 8.4), 6.90 (1H, d, J=8.8 Hz), 6.95 (1H, d, J=4.8 Hz), 7.03 (1H, d, J=2.4 Hz), 7.14 (1H, dd, J=2.8, 9.2 Hz), 7.58 (1H, d, J=4.8 Hz), 7.62 (1H, dd, J=1.6, 8.8 Hz), 7.78 (1H, d, J=8.8 Hz), 7.87 (1H, d, J=9.2 Hz), 8.39 (1H, s).

Production Example 5-12 t-Butyl 5'-amino-2'-(6-cyano-2-naphthyloxy)-4,5-dimethoxy-1,1'-biphenyl-2-carboxylate $^1$H-NMR (d$_6$-DMSO) δ: 1.28 (9H, s), 3.47 (3H, s), 3.66 (3H, s), 5.11 (1H, brs), 6.52 (1H, d, J=2.4 Hz), 6.62 (1H, dd, J=2.4, 8.4 Hz), 6.73 (1H, s), 6.87 (1H, d, J=8.8 Hz), 7.08 (1H, d, J=2.8 Hz), 7.12 (1H, s), 7.14 (1H, dd, J=2.4, 9.2 Hz), 7.61 (1H, dd, J=1.6, 8.4 Hz), 7.83 (2H, t, J=8.8 Hz), 8.37 (1H, s).

Production Example 5-13 t-Butyl 5'-amino-2'-(6-cyano-2-naphthyloxy)-4-(2-methylpropoxy)-1,1'-biphenyl-2-carboxylate $^1$H-NMR (d$_6$-DMSO) δ: 0.87 (6H, d, J=6.8 Hz), 1.32 (9H, s), 1.86 (1H, m), 3.63 (2H, d, J=6.8 Hz), 5.11 (1H, brs), 6.52 (1H, d, J=2.8 Hz), 6.61 (1H, dd, J=3.2, 8.4 Hz), 6.86 (1H, d, J=8.4 Hz), 6.88 (1H, dd, J=2.8, 8.4 Hz), 7.00 (1H, d, J=2.4 Hz), 7.05 (1H, d, J=2.8 Hz), 7.11 (1H, dd, J=2.4, 8.8 Hz), 7.13 (1H, d, J=8.4 Hz), 7.60 (1H, dd, J=1.6, 8.4 Hz), 7.79 (1H, d, J=8.4 Hz), 7.84 (1H, d, J=9.2 Hz), 8.36 (1H, s).

Production Example 5-14

Methyl 5'-amino-2'-(6-cyano-2-naphthyloxy)-4-[(2-methylpropyl)carbamoyl]-1,1'-biphenyl-2-carboxylate $^1$H-NMR (CDCl$_3$+d$_6$-DMSO) δ: 0.96 (6H, d, J=7.2 Hz), 1.54–1.62 (1H, m), 2.84–2.87 (2H, m), 3.44 (3H, s), 6.44 (1H, d, J=2.8 Hz), 6.47 (1H, dd, J=2.4, 8.4 Hz), 6.62 (1H, d, J=8.4 Hz), 6.67 (1H, d, J=2.8 Hz), 6.83 (1H, dd, J=2.6, 9.0 Hz), 7.09 (1H, d, J=8.0 Hz), 7.18 (1H, dd, J=1.4, 8.6 Hz), 7.32 (1H, d, J=8.8 Hz), 7.40 (1H, d, J=8.8 Hz), 7.47 (1H, brs), 7.58 (1H, dd, J=2.0, 8.4 Hz), 7.79 (1H, s), 7.91 (1H, d, J=1.6 Hz).

Production Example 6-1

2-(6-bromo-2-naphthyloxy)-4-nitrobenzonitrile

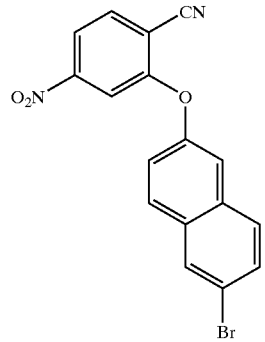

After heating to reflux 2-fluoro-4-nitrobenzonitrile (1 g), 6-bromo-2-naphthol (1.41 g), potassium fluoride/alumina (0.7 g) and 18-crown-6 (0.16 g) in acetonitrile, the mixture was reacted for 12 hours. It was then cooled to room temperature, the insoluble portion was filtered using celite, the ethyl acetate layer was washed with water and saturated saline and then dried over magnesium sulfate, and the solvent was distilled off. Methanol was added to the residue for crystallization to obtain 1.43 g of 2-(6-bromo-2-naphthyloxy)-4-nitrobenzonitrile.

$^1$H-NMR (CDCl$_3$) δ: 7.31 (1H, dd, J=2.4, 8.8 Hz), 7.54 (1H, d, J=2.0 Hz), 7.62–7.70 (3H, m), 7.88 (1H, s), 7.90 (1H, s), 8.01 (1H, dd, J=2.0, 8.4 Hz), 8.08 (1H, s).

Production Example 6-2 t-Butyl 2-(6-bromo-2-naphthyloxy)-4-nitrobenzoate

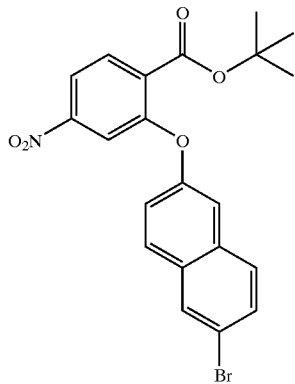

The compound (2-(6-bromo-2-naphthyloxy)-4-nitrobenzonitrile) (1 g) obtained in a previous production example was dissolved in acetic acid (20 ml) and then concentrated sulfuric acid (5 ml) was slowly added. After heating to reflux for 12 hours, the mixture was cooled to room temperature and ice water was added to obtain a precipitate. This was dissolved in toluene without purification and subjected to the same process as in Production Examples 1 to obtain t-butyl 2-(6-bromo-2-naphthyloxy)-4-nitrobenzoate.

$^{1}$H-NMR (CDCl$_3$) δ: 1.41 (9H, s), 7.20 (1H, d, J=2.8 Hz), 7.28 (1H, dd, J=2.8, 9.2 Hz), 7.53–7.59 (2H, m), 7.78–7.84 (2H, m), 7.96–8.06 (3H, m).

Production Example 6-3 t-Butyl 2-(6-cyano-2-naphthyloxy)-4-nitrobenzoate

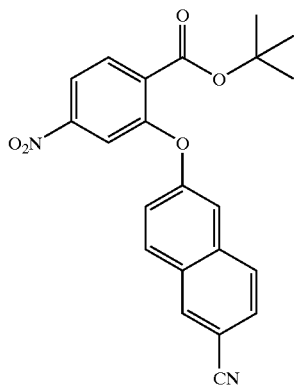

The compound (t-butyl 2-(6-bromo-2-naphthyloxy)-4-nitrobenzoate) (1.78 g) obtained in a previous production example, zinc cyanide (0.33 g) and tetrakis(triphenylphosphine)palladium (0) (690 mg) were reacted for 12 hours at 100° C. in N,N-dimethylformamide. After cooling to room temperature, toluene and ethyl acetate were added, the organic layer was washed with 2 N ammonia water and saturated saline and dried over magnesium sulfate, and the solvent was distilled off. The residue was purified by silica gel chromatography (300 g, hexane:ethyl acetate=6:1) to obtain 1.14 g of t-butyl 2-(6-cyano-2-naphthyloxy)-4-nitrobenzoate.

$^{1}$H-NMR (CDCl$_3$) δ: 1.37 (9H, s), 7.18 (1H, d, J=2.8 Hz), 7.39 (1H, dd, J=2.4, 8.8 Hz), 7.60 (1H, dd, J=1.6, 8.4 Hz), 7.75 (1H, d, J=8.4 Hz), 7.92 (1H, d, J=2.4 Hz), 7.94 (1H, d, J=9.2 Hz), 8.03 (1H, d, J=8.8 Hz), 8.12 (1H, dd, J=2.0, 8.4 Hz), 8.22 (1H, s).

Production Example 6-4 t-Butyl 4-amino-2-(6-cyano-2-naphthyloxy)benzoate

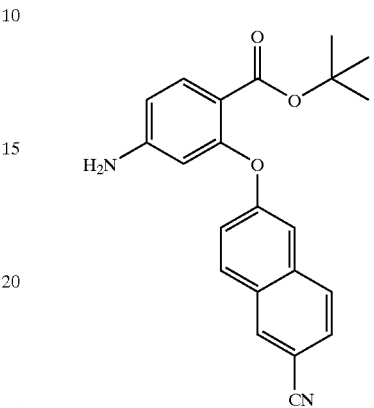

The compound (t-butyl 2-(6-cyano-2-naphthyloxy)-4-nitrobenzoate) obtained in a previous production example was treated by the same process as in Production Example 5-1 to obtain t-butyl 4-amino-2-(6-cyano-2-naphthyloxy)benzoate.

$^{1}$H-NMR (d$_6$-DMSO) δ: 1.63 (9H , s), 6.05 (1H, d, J=4.8 Hz), 6.23 (1H, d, J=2.4 Hz), 6.49 (1H, dd, J=2.4, 8.8 Hz), 7.14 (1H, z, d, J=2.8 Hz), 7.37 (1H, dd, J=2.4, 9.2 Hz), 7.62 (1H, d, J=8.4 Hz), 7.67 (1H, dd, J=1.6, 8.8 Hz), 7.94 (1H, d, J=8.8 Hz), 8.05 (1H, d, J=9.2 Hz), 8.49 (1H, s).

Production Examples 7-1 and 7-2

Compounds (Ia) represented by the formula HO—Ar—CN (wherein Ar represents the Ar groups in the following table) were used for reaction in the same manner as Production Example 2-1 to obtain compounds for Production Examples 7-1 and 7-2.

TABLE 5

| Example | Ar |
|---------|----|
| 7-1 | naphthalene-2,6-diyl |
| 7-2 | 1,4-phenylene |

Production Example 7-1

3-(6-cyano-2-naphthyloxy)-4-nitrotoluene $^1$H-NMR (CDCl$_3$) δ: 2.41 (3H, s), 6.97–6.98 (1H, m), 7.14–7.17 (1H, m), 7.23 (1H, d, J=2.8 Hz), 7.39 (1H, dd, J=2.8, 8.8 Hz), 7.59 (1H, dd, J=1.6, 8.6 Hz), 7.76 (1H, d, J=8.8 Hz), 7.92 (1H, d, J=8.8 Hz), 7.99 (1H, d, J=8.4 Hz), 8.21 (1H, d, J=0.8 Hz).

Production Example 7-2

3-(4-cyanophenoxy)-4-nitrotoluene $^1$H-NMR (CDCl$_3$) δ: 2.44 (3H, s), 6.98–7.02 (3H, m), 7.17–7.19 (1H, m), 7.63 (2H, dd, J=2.0, 6.8 Hz), 7.99 (1H, d, J=8.4 Hz).

Production Examples 8-1 and 8-2

The two compounds obtained above, (3-(6-cyano-2-naphthyloxy)-4-nitrotoluene and 3-(4-cyanophenoxy)-4-nitrotoluene) were used for the same reaction as in Production Example 5-1 to obtain compounds for Production Examples 8-1 and 8-2, respectively.

TABLE 6

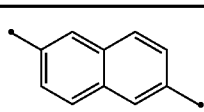

| Example | Ar |
|---|---|
| 8-1 | 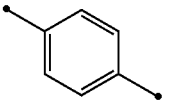 |
| 8-2 | 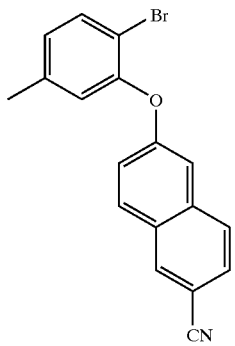 |

Production Example 8-1

4-amino-3-(6-cyano-2-naphthyloxy)toluene $^1$H-NMR (CDCl$_3$) δ: 2.25 (3H, s), 3.61 (2H, brs), 6.94–6.98 (2H, m), 7.08 (1H, d, J=2.4 Hz), 7.37 (1H, dd, J=2.4, 8.8 Hz), 7.54–7.58 (2H, m), 7.72 (1H, d, J=8.8 Hz), 7.88 (1H, d, J=8.8 Hz), 8.19 (1H, d, J=0.8 Hz).

Production Example 8-2

4-amino-3-(4-cyanophenoxy)toluene $^1$H-NMR (CDCl$_3$) δ: 2.24 (3H, s), 6.74–6.75 (2H, m), 6.77–6.90 (1H, m), 6.98 (2H, dd, J=2.0, 6.8 Hz), 7.58 (2H, dd, J=2.0, 6.8 Hz).

Production Example 9-1

4-bromo-3-(6-cyano-2-naphthyloxy)toluene

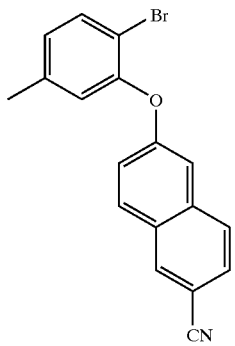

After adding t-butyl nitrite (90 mL) and copper (II) bromide (142 mg) to a mixture of the compound (4-amino-3-(6-cyano-2-naphthyloxy)toluene) (760 mg) obtained above and 5 mL of acetonitrile at a room temperature, the mixture was stirred for one hour at 50° C. The reaction solution was returned to room temperature, water and ammonia water were added and extraction was performed with ethyl acetate. The organic layer was washed with saturated saline, dried over anhydrous magnesium sulfate, and concentrated under reduced pressure. The residue was purified by silica gel chromatography (hexane:ethyl acetate= 20:1) to obtain 200 mg of the corresponding bromo compound (93% yield).

$^1$H-NMR (CDCl$_3$) δ: 2.25 (3H, s), 3.61 (2H, brs), 6.79–6.81 (2H, m), 6.89–6.92 (1H, m), 7.15 (1H, d, J=2.8 Hz), 7.39 (1H, dd, J=8.8, 2.8 Hz), 7.54 (1H, dd, J=8.4, 1.6 Hz), 7.71 (1H, d, J=8.8 Hz), 7.86 (1H, d, J=8.8 Hz), 8.17 (1H, s).

Production Example 9-2

4-bromo-3-(4-cyanophenoxy)toluene

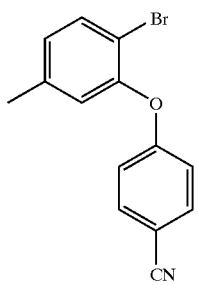

The compound (4-amino-3-(4-cyanophenoxy)toluene) obtained above was used for the same reaction as in Production Example 9-1 to obtain the title compound.

$^1$H-NMR (CDCl$_3$) δ: 2.32 (3H, s), 6.91–6.98 (4H, m), 7.52 (1H, d, J=8.0 Hz), 7.58–7.62 (2H, m).

Production Examples 10-1 and 10-2

The two compounds obtained above, (4-bromo-3-(6-cyano-2-naphthyloxy)toluene and 4-bromo-3-(4-cyanophenoxy)toluene) were used for the same reaction as in Production Example 3-9 to obtain compounds for Production Examples 10-1 and 10-2, respectively.

TABLE 7

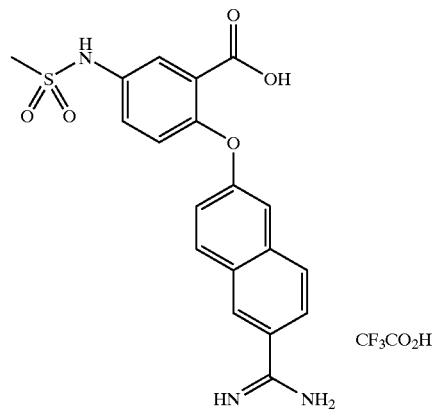

| Example | Ar |
|---|---|
| 10-1 | (2,6-naphthalenediyl) |
| 10-2 | (1,4-phenylene) |

Production Example 10-1

Methyl 2'-(6-cyano-2-naphthyloxy)-4-(2-methylpropylcarbamoyl)-4'-methyl-1,1'-biphenyl-2-carboxylate $^1$H-NMR (CDCl$_3$) δ: 0.95 (6H, d, J=6.4 Hz), 1.83–1.95 (1H, m), 2.40 (3H, s), 3.22–3.30 (2H, m), 3.73 (3H, s), 6.92 (1H, s), 7.02 (1H, d, J=8.8 Hz), 7.06 (1H, d, J=2.0 Hz), 7.13–7.20 (2H, m), 7.29 (1H, d, J=7.6 Hz), 7.42 (1H, d, J=8.0 Hz), 7.50 (1H, dd, J=8.8, 1.6 Hz), 7.64 (1H, d, J=8.4 Hz), 7.71 (1H, d, J=8.8 Hz), 7.85 (1H, d, J=8.2, 2.0 Hz), 8.09 (1H, s), 8.12 (1H, d, J=2.0 Hz).

Production Example 10-2

Methyl 2'-(4-cyanophenoxy)-4-(2-methylpropylcarbamoyl)-4'-methyl-1,1'-biphenyl-2-carboxylate $^1$H-NMR (CDCl$_3$) δ: 0.97 (6H, d, J=6.8 Hz), 1.87–1.95 (1H, m), 3.28 (2H, dd, J=6.8, 6.0 Hz), 3.72 (3H, s), 6.80–6.83 (2H, m), 6.88 (1H, d, J=1.2 Hz), 7.15 (1H, dd, J=7.2, 1.2 Hz), 7.26 (1H, d, J=7.2 Hz), 7.36 (1H, d, J=8.0 Hz), 7.42–7.46 (2H, m), 7.88 (1H, dd, J=8.0, 1.2 Hz), 8.14 (1H, d, J=1.2 Hz).

Example 1-1

2-(6-amidino-2-naphthyloxy)-5-methanesulfonyl-aminobenzoic acid trifluoroacetate Methanesulfonyl chloride (8 mg) was added to a pyridine solution containing the compound (t-butyl 5-amino-2-(6-cyano-2-naphthyloxy)benzoate) (20 mg) obtained in a previous production example, and reaction was conducted at 50° C. for 1 hour. The reaction solution was concentrated a saturated sodium bicarbonate solution was added to the residue, and extraction was performed with ethyl acetate. After freezing the aqueous layer with ethanol-dry ice, the ethyl acetate layer was decanted and the solvent was distilled off. Hydroxyamine hydrochloride (14 mg) and potassium carbonate (15 mg) were added to the obtained residue, and reaction was conducted for 12 hours at 60° C. in ethanol:water (2:1, 1 ml). After cooling to room temperature, the reaction solution was concentrated saturated saline was added to the residue, and extraction was performed with ethyl acetate. After freezing the aqueous layer with ethanol-dry ice, the ethyl acetate layer was decanted and the solvent was distilled off. The obtained residue was dissolved in acetic acid (1 ml), acetic anhydride (8 mg) was added and reaction was conducted at room temperature for 15 minutes. Next, 10% palladium-carbon (1 mg) was added thereto and catalytic reduction was carried out for 6 hours under ordinary pressure. The catalyst was then filtered off using celite, and the filtrate was concentrated. The residue was dissolved in trifluoroacetic acid-:dichloromethane (1:1, 1 ml) and reaction was conducted at room temperature for 90 minutes. The solvent was distilled off and the residue was purified by LC-MS (from 1% acetonitrile/water (0.1% trifluoroacetic acid) to 80% acetonitrile/water (0.1% trifluoroacetic acid), flow rate: 20 ml/min) to obtain 11.4 mg of 2-(6-amidino-2-naphthyloxy)-5-[(methylsulfonyl)amino]benzoic acid trifluoroacetate. R$_T$=6.68 min, ESI-MS (m/z): 400.17 (M+1)$^+$.

Examples 1-2 to 1-69

The compounds {t-butyl 5-amino-2-(6-cyano-2-naphthyloxy)benzoate, t-butyl 5-amino-2-(4-cyanophenoxy)benzoate, t-butyl 5-amino-2-(3-cyanophenoxy)benzoate, t-butyl 5-amino-2-(4-cyano-1,1'-biphenyl-4'-yloxy)benzoate, t-butyl 5-amino-2-[2-(4-cyanophenyl)ethoxy]benzoate, t-butyl 5'-amino-2'-(6-cyano-2-naphthyloxy)-1,1'-biphenyl-2-carboxylate, t-butyl 5'-amino-2'-(4-cyanophenoxy)-1,1'-biphenyl-2-carboxylate, t-butyl 5'-amino-2'-(6-cyano-2-naphthyloxy)-1,1'-biphenyl- 3-carboxylate, t-butyl 5'-amino-2'-(4-cyanophenoxy)-1,1'-biphenyl-3-carboxylate, t-butyl 3-[5-amino-2-(6-cyano-2-naphthyloxy)phenyl]-naphthalene-2-carboxylate, t-butyl 3-[5-amino-2-(6-cyano-2-naphthyloxy)phenyl]-thiophene-2-carboxylate, t-butyl 5'-amino-2'-(6-cyano-2-naphthyloxy)-4,5-dimethoxy-1,1'-biphenyl-2-carboxylate and t-butyl 5'-amino-2'-(6-cyano-2-naphthyloxy)-4-(2-methylpropoxy)-1,1'-biphenyl-2-carboxylate} obtained in the previous production examples, and sulfonylchloride derivatives represented by the following formula (Ib):

$$R^1-SO_2-Cl$$

(where $R^1$ represents the respective $R^1$ groups in Tables 8 to 12) were used for reaction in the same manner as in Example 1-1 to obtain compounds for Examples 1-2 to 1-69, respectively.

TABLE 8

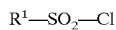

| EXAMPLE | Ar | R¹ | Y | $R_T$(min) | $(M+1)^+$ |
|---------|-----|-----|-----|-----|-----|
| 1-2 | (2,6-naphthyl) | (4-methoxyphenyl) | COOH | 8.92 | 492.1 |
| 1-3 | ↑ | (4-fluorophenyl) | ↑ | 8.88 | 480.1 |
| 1-4 | ↑ | (naphthyl) | ↑ | 9.44 | 512.1 |
| 1-5 | ↑ | (2,3-dichlorophenyl) | ↑ | 9.41 | 530.0 |
| 1-6 | ↑ | (thiophene-phenylsulfonyl) | ↑ | 8.51 | 608.2 |
| 1-7 | ↑ | (3-nitrophenyl) | ↑ | 8.48 | 507.2 |
| 1-8 | (1,4-phenyl) | (4-methoxyphenyl) | ↑ | 7.19 | 442.1 |
| 1-9 | ↑ | (4-fluorophenyl) | ↑ | 7.08 | 430.1 |

TABLE 8-continued

| EXAMPLE | Ar | R¹ | Y | $R_T$(min) | $(M + 1)^+$ |
|---|---|---|---|---|---|
| 1-10 | ↑ | 2-naphthyl | ↑ | 7.95 | 462.2 |
| 1-11 | ↑ | 5-(phenylsulfonyl)thiophen-2-yl | ↑ | 7.89 | 558.2 |
| 1-12 | ↑ | Me | ↑ | 5.62 | 350.2 |
| 1-13 | 1,3-phenylene | 4-methoxyphenyl | ↑ | 7.69 | 442.2 |
| 1-14 | ↑ | 4-fluorophenyl | ↑ | 7.69 | 430.2 |

TABLE 9

| EXAMPLE | Ar | R¹ | Y | $R_T$(min) | $(M + 1)^+$ |
|---|---|---|---|---|---|
| 1-15 | ↑ | 2-naphthyl | ↑ | 8.46 | 462.2 |
| 1-16 | ↑ | 5-(phenylsulfonyl)thiophen-2-yl | ↑ | 8.14 | 558.2 |
| 1-17 | 4,4'-biphenylene | 4-fluorophenyl | ↑ | 8.75 | 506.2 |

TABLE 9-continued
| EXAMPLE | Ar | R¹ | Y | $R_T$(min) | $(M + 1)^+$ |
|---|---|---|---|---|---|
| 1-18 | ↑ | 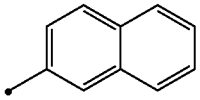 | ↑ | 9.30 | 538.3 |
| 1-19 | ↑ | 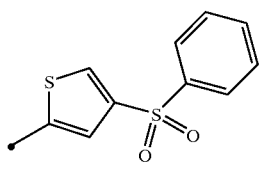 | ↑ | 9.48 | 634.3 |
| 1-20 | ↑ | Me | ↑ | 7.25 | 426.3 |
| 1-21 | 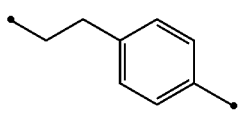 | 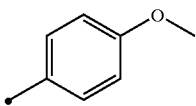 | ↑ | 7.69 | 469.9 |
| 1-22 | ↑ | 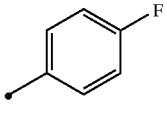 | ↑ | 7.74 | 458.0 |
| 1-23 | ↑ | 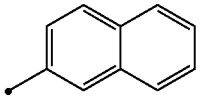 | ↑ | 8.51 | 490.1 |
| 1-24 | ↑ | 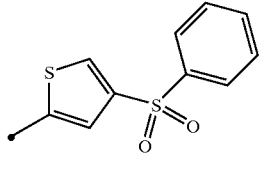 | ↑ | 9.06 | 586.1 |
| 1-25 | ↑ | Me | ↑ | 6.10 | 378.1 |
| 1-26 | 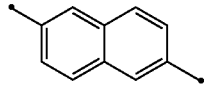 | 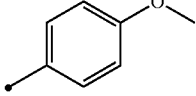 | 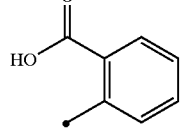 | 9.07 | 567.9 |
| 1-27 | ↑ | 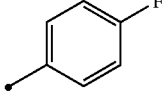 | ↑ | 9.13 | 555.9 |
| 1-28 | ↑ | 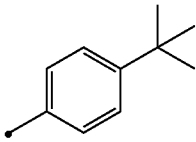 | ↑ | 10.20 | 594.1 |

TABLE 10

| EXAMPLE | Ar | R¹ | Y | $R_T$(min) | $(M+1)^+$ |
|---|---|---|---|---|---|
| 1-29 | ↑ | 4-(acetamido)phenyl | ↑ | 8.30 | 594.9 |
| 1-30 | ↑ | 5-chlorothiophen-2-yl | ↑ | 10.37 | 577.9 |
| 1-31 | ↑ | 5-chloro-3-methylbenzothiophen-2-yl | ↑ | 11.26 | 641.9 |
| 1-32 | ↑ | 1-methylimidazol-4-yl | ↑ | 7.93 | 542.0 |
| 1-33 | ↑ | 4-(methylsulfonyl)phenyl | ↑ | 9.45 | 615.9 |
| 1-34 | ↑ | 3,4-dimethoxyphenyl | ↑ | 9.47 | 578.0 |
| 1-35 | ↑ | 3-carboxyphenyl | ↑ | 9.27 | 582.0 |
| 1-36 | ↑ | 4-(trifluoromethoxy)phenyl | ↑ | 10.16 | 622.0 |
| 1-37 | ↑ | 4-(trifluoromethyl)phenyl | ↑ | 10.00 | 606.0 |
| 1-38 | ↑ | 3-chlorophenyl | ↑ | 9.63 | 572.0 |
| 1-39 | ↑ | 2-acetyl-1,2,3,4-tetrahydroisoquinolin-7-yl | ↑ | 8.68 | 635.1 |
| 1-40 | ↑ | 3-chloro-4-methylphenyl | ↑ | 10.00 | 585.9 |
| 1-41 | ↑ | 3-fluoro-4-methoxyphenyl | ↑ | 9.45 | 586.0 |
| 1-42 | ↑ | Me | ↑ | 7.84 | 475.9 |

TABLE 11

| EXAMPLE | Ar | R¹ | Y | $R_T$(min) | $(M+1)^+$ |
|---|---|---|---|---|---|
| 1-43 | 1,4-phenylene | 4-methoxyphenyl | ↑ | 8.42 | 518.0 |
| 1-44 | ↑ | phenyl | ↑ | 8.61 | 506.0 |
| 1-45 | ↑ | Me | ↑ | 6.94 | 426.0 |

TABLE 11-continued
| EXAMPLE | Ar | R¹ | Y | $R_T$(min) | $(M + 1)^+$ |
|---|---|---|---|---|---|
| 1-46 | 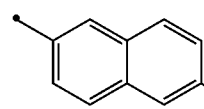 | 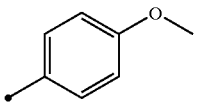 | 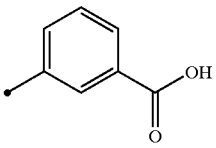 | 9.61 | 567.9 |
| 1-47 | ↑ | 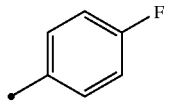 | ↑ | 9.78 | 555.9 |
| 1-48 | ↑ | 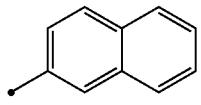 | ↑ | 10.22 | 588.0 |
| 1-49 | ↑ | Me | ↑ | 8.50 | 476.1 |
| 1-50 | 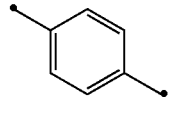 | 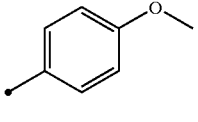 | ↑ | 9.17 | 517.9 |
| 1-51 | ↑ | 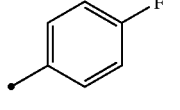 | ↑ | 9.27 | 505.9 |
| 1-52 | ↑ | 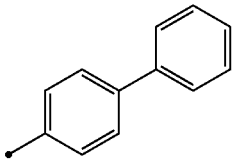 | ↑ | 10.13 | 564.0 |
| 1-53 | ↑ | Me | ↑ | 7.67 | 425.9 |
| 1-54 | 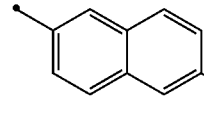 | 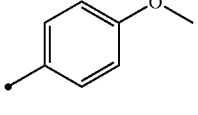 | 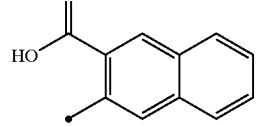 | 10.29 | 617.9 |
| 1-55 | ↑ | 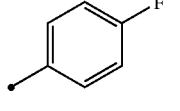 | ↑ | 10.51 | 606.0 |
| 1-56 | ↑ | 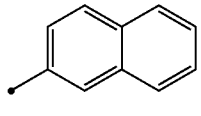 | ↑ | 10.84 | 638.0 |

TABLE 12

| EXAMPLE | Ar | R¹ | Y | R_T(min) | (M + 1)⁺ |
|---|---|---|---|---|---|
| 1-57 | ↑ | Me | ↑ | 9.21 | 526.0 |
| 1-58 | ↑ | 4-methoxyphenyl | 3-carboxythiophen-2-yl (HOOC-thiophene) | 9.49 | 574.00 |
| 1-59 | ↑ | 4-fluorophenyl | ↑ | 9.60 | 561.9 |
| 1-60 | ↑ | naphthalen-2-yl | ↑ | 10.07 | 594.0 |
| 1-61 | ↑ | Me | ↑ | 8.28 | 481.9 |
| 1-62 | ↑ | 3-fluoro-4-methoxyphenyl | 2-carboxy-4,5-dimethoxyphenyl | 9.21 | 646.0 |
| 1-63 | ↑ | 3-chloro-4-methylphenyl | ↑ | 9.89 | 646.0 |
| 1-64 | ↑ | 2-methylphenyl | ↑ | 9.23 | 612.1 |
| 1-65 | ↑ | Me | ↑ | 7.91 | 536.0 |
| 1-66 | ↑ | 3-fluoro-4-methoxyphenyl | 2-carboxy-4-isobutoxyphenyl | 10.71 | 658.1 |
| 1-67 | ↑ | 3-chloro-4-methylphenyl | ↑ | 11.45 | 658.1 |
| 1-68 | ↑ | 2-methylphenyl | ↑ | 10.84 | 624.1 |
| 1-69 | ↑ | Me | ↑ | 9.67 | 548.1 |

TABLE 13

| Example | Compound name |
|---|---|
| 1-2 | 2-(6-amidino-2-naphthyloxy)-5-(4-methoxybenzenesulfonyl) aminobenzoic acid trifluoroacetate |
| 1-3 | 2-(6-amidino-2-naphthyloxy)-5-(4-fluorobenzenesulfonyl) aminobenzoic acid trifluoroacetate |
| 1-4 | 2-(6-amidino-2-naphthyloxy)-5-(2-naphthalenesulfonyl) aminobenzoic acid trifluoroacetate |
| 1-5 | 2-(6-amidino-2-naphthyloxy)-5-(2,3-dichlorobenzene sulfonyl)aminobenzoic acid trifluoroacetate |
| 1-6 | 2-(6-amidino-2-naphthyloxy)-5-[4-(phenylsulfonyl) thiophene-2-sulfonyl]aminobenzoic acid trifluoroacetate |
| 1-7 | 2-(6-amidino-2-naphthyloxy)-5-(3-nitrobenzenesulfonyl) aminobenzoic acid trifluoroacetate |
| 1-8 | 2-(4-amidinophenoxy)-5-(4-methoxybenzenesulfonyl) aminobenzoic acid trifluoroacetate |
| 1-9 | 2-(4-amidinophenoxy)-5-(4-fluorobenzenesulfonyl) aminobenzoic acid trifluoroacetate |
| 1-10 | 2-(4-amidinophenoxy)-5-(2-naphthalenesulfonyl)aminobenzoic acid trifluoroacetate |
| 1-11 | 2-(4-amidinophenoxy)-5-[4-(phenylsulfonyl)thiophene-2-sulfonyl]aminobenzoic acid trifluoroacetate |
| 1-12 | 2-(4-amidinophenoxy)-5-methanesulfonylaminobenzoic acid trifluoroacetate |
| 1-13 | 2-(3-amidinophenoxy)-5-(4-methoxybenzenesulfonyl) aminobenzoic acid trifluoroacetate |
| 1-14 | 2-(3-amidinophenoxy)-5-(4-fluorobenzenesulfonyl) aminobenzoic acid trifluoroacetate |

TABLE 14

| Example | Compound name |
|---|---|
| 1-15 | 2-(3-amidinophenoxy)-5-(2-naphthalenesulfonyl) aminobenzoic acid trifluoroacetate |
| 1-16 | 2-(3-amidinophenoxy)-5-[4-(phenylsulfonyl) thiophene-2-sulfonyl]aminobenzoic acid trifluoroacetate |
| 1-17 | 2-(4'-amidino-4-biphenyloxy)-5-(4-fluorobenzenesulfonyl) aminobenzoic acid trifluoroacetate |
| 1-18 | 2-(4'-amidino-4-biphenyloxy)-5-(2-naphthalenesulfonyl) aminobenzoic acid trifluoroacetate |
| 1-19 | 2-(4'-amidino-4-biphenyloxy)-5-[4(phenylsulfonyl) thiophene-2-sulfonyl]aminobenzoic acid trifluoroacetate |
| 1-20 | 2-(4'-amidino-4-biphenyloxy)-5-methanesulfonylaminobenzoic acid trifluoroacetate |
| 1-21 | 2-[2-(4-amidinophenyl)ethoxy]-5-(4-methoxybenzenesulfonyl) aminobenzoic acid trifluoroacetate |
| 1-22 | 2-[2-(4-amidinophenyl)ethoxy]-5-(4-fluorobenzenesulfonyl) aminobenzoic acid trifluoroacetate |
| 1-23 | 2-[2-(4-amidinophenyl)ethoxy]-5-(2-naphthalenesulfonyl) aminobenzoic acid trifluoroacetate |
| 1-24 | 2-[2-(4-amidinophenyl)ethoxy]-5-[4-(phenylsulfonyl) thiophene-2-sulfonyl]aminobenzoic acid trifluoroacetate |
| 1-25 | 2-[2-(4-amidinophenyl)ethoxy]-5-methanesulfonyl aminobenzoic acid trifluoroacetate |
| 1-26 | 2'-(6-amidino-2-naphthyloxy)-5'-(4-methoxybenzenesulfonyl) amino-1,1'-biphenyl-2-carboxylic acid trifluoroacetate |
| 1-27 | 2'-(6-amidino-2-naphthyloxy)-5'-(4-fluorobenzenesulfonyl) amino-1,1'-biphenyl-2-carboxylic acid trifluoroacetate |

TABLE 15

| Example | Compound name |
|---|---|
| 1-28 | 2'-(6-amidino-2-naphthyloxy)-5'-(4-t-butylbenzenesulfonyl) amino-1,1'-biphenyl-2-carboxylic acid trifluoroacetate |
| 1-29 | 2'-(6-amidino-2-naphthyloxy)-5'-(4-acetamidobenzene sulfonyl)amino-1,1'-biphenyl-2-carboxylic acid trifluoroacetate |
| 1-30 | 2'-(6-amidino-2-naphthyloxy)-5'-(5-chlorothiophene-2-sulfonyl)amino-1,1'-biphenyl-2-carboxylic acid trifluoroacetate |
| 1-31 | 2'-(6-amidino-2-naphthyloxy)-5'-(5-chloro-3-methylbenzo[b]thiophene-2-sulfonyl)amino-1,1'-biphenyl-2-carboxylic acid trifluoroacetate |

TABLE 15-continued

| Example | Compound name |
|---|---|
| 1-32 | 2'-(6-amidino-2-naphthyloxy)-5'-(1-methylimidazole-4-sulfonyl)amino-1,1'-biphenyl-2-carboxylic acid trifluoroacetate |
| 1-33 | 2'-(6-amidino-2-naphthyloxy)-5'-(4-methanesulfonylbenzene sulfonyl)amino-1,1'-biphenyl-2-carboxylic acid trifluoroacetate |
| 1-34 | 2'-(6-amidino-2-naphthyloxy)-5'-(3,4-dimethoxybenzene sulfonyl)amino-1,1'-biphenyl-2-carboxylic acid trifluoroacetate |
| 1-35 | 2'-(6-amidino-2-naphthyloxy)-5'-(3-carboxylbenzene sulfonyl)amino-1,1'-biphenyl-2-carboxylic acid trifluoroacetate |
| 1-36 | 2'-(6-amidino-2-naphthyloxy)-5'-(4-trifluoromethoxybenzene sulfonyl)amino-1,1'-biphenyl-2-carboxylic acid trifluoroacetate |

TABLE 16

| Example | Compound name |
|---|---|
| 1-37 | 2'-(6-amidino-2-naphthyloxy)-5'-(4-trifluoromethylbenzene sulfonyl)amino-1,1'-biphenyl-2-carboxylic acid trifluoroacetate |
| 1-38 | 2'-(6-amidino-2-naphthyloxy)-5'-(3-chlorobenzenesulfonyl) amino-1,1'-biphenyl-2-carboxylic acid trifluoroacetate |
| 1-39 | 2'-(6-amidino-2-naphthyloxy)-5'-[1,2,3,4-tetrafluoro-2-(acetyl)isoquinoline-7-sulfonyl)amino-1,1'-biphenyl-2-carboxylic acid trifluoroacetate |
| 1-40 | 2'-(6-amidino-2-naphthyloxy)-5'-(3-chloro-4-methylbenzenesulfonyl)amino-1,1'-biphenyl-2-carboxylic acid trifluoroacetate |
| 1-41 | 2'-(6-amidino-2-naphthyloxy)-5'-(3-fluoro-4-methoxybenzenesulfonyl)amino-1,1'-biphenyl-2-carboxylic acid trifluoroacetate |
| 1-42 | 2'-(6-amidino-2-naphthyloxy)-5'-methanesulfonylamino-1,1'-biphenyl-2-carboxylic acid trifluoroacetate |
| 1-43 | 2'-(4-amidinophenoxy)-5'-(4-methoxybenzenesulfonyl)amino-1,1'-biphenyl-2-carboxylic acid trifluoroacetate |
| 1-44 | 2'-(4-amidinophenoxy)-5'-benzenesulfonylamino-1,1'-biphenyl-2-carboxylic acid trifluoroacetate |
| 1-45 | 2'-(4-amidinophenoxy)-5'-methanesulfonylamino-1,1'-biphenyl-2-carboxylic acid trifluoroacetate |
| 1-46 | 2'-(6-amidino-2-naphthyloxy)-5'-(4-methoxybenzenesulfonyl) amino-1,1'-biphenyl-3-carboxylic acid trifluoroacetate |
| 1-47 | 2'-(6-amidino-2-naphthyloxy)-5'-(4-fluorobenzenesulfonyl) amino-1,1'-biphenyl-3-carboxylic acid trifluoroacetate |

TABLE 17

| Example | Compound name |
|---|---|
| 1-48 | 2'-(6-amidino-2-naphthyloxy)-5'-(2-naphthalenesulfonyl) amino-1,1'-biphenyl-3-carboxylic acid trifluoroacetate |
| 1-49 | 2'-(6-amidino-2-naphthyloxy)-5'-methanesulfonylamino-1,1'-biphenyl-3-carboxylic acid trifluoroacetate |
| 1-50 | 2'-(4-amidinophenoxy)-5'-(4-methoxybenzenesulfonyl)amino-1,1'-biphenyl-3-carboxylic acid trifluoroacetate |
| 1-51 | 2'-(4-amidinophenoxy-5'-benzenesulfonylamino-1,1'-biphenyl-3-carboxylic acid trifluoroacetate |
| 1-52 | 2'-(4-amidinophenoxy-5'-(4-biphenylsulfonyl)amino-1,1' biphenyl-3-carboxylic acid trifluoroacetate |
| 1-53 | 2'-(4-amidinophenoxy)-5'-methanesulfonylamino-1,1'-biphenyl-3-carboxylic acid trifluoroacetate |
| 1-54 | 3-[2-(6-amidino-2-naphthyloxy)-5-(4-methoxybenzene sulfonyl)amino-phenyl]-naphthalene-2-carboxylic acid trifluoroacetate |
| 1-55 | 3-[2-(6-amidino-2-naphthyloxy)-5-(4-fluorobenzenesulfonyl) amino-phenyl]-naphthalene-2-carboxylic acid trifluoroacetate |
| 1-56 | 3-[2-(6-amidino-2-naphthyloxy)-5-(2-naphthalenesulfonyl) amino-phenyl]-naphthalene-2-carboxylic acid trifluoroacetate |

TABLE 17-continued

| Example | Compound name |
|---|---|
| 1-57 | 3-[2-(6-amidino-2-naphthyloxy)-5-methanesulfonylamino-phenyl]-naphthalene-2-carboxylic acid trifluoroacetate |
| 1-58 | 3-[2-(6-cyano-2-naphthyloxy)-5-(4-methoxybenzenesulfonyl)amino-phenyl]-thiophene-2-carboxylic acid trifluoroacetate |

TABLE 18

| Example | Compound name |
|---|---|
| 1-59 | 3-[2-(6-cyano-2-naphthyloxy)-5-(4-fluorobenzenesulfonyl)amino-phenyl]-thiophene-2-carboxylic acid trifluoroacetate |
| 1-60 | 3-[2-(6-cyano-2-naphthyloxy)-5-(2-naphthalenesulfonyl)amino-phenyl]-thiophene-2-carboxylic acid trifluoroacetate |
| 1-61 | 3-[2-(6-cyano-2-naphthyloxy)-5-methanesulfonylamino-phenyl]-thiophene-2-carboxylic acid trifluoroacetate |
| 1-62 | 2'-(6-cyano-2-naphthyloxy)-5'-(3-fluoro-4-methoxybenzene sulfonyl)amino-4,5-dimethoxy-1,1'-biphenyl-2-carboxylic acid trifluoroacetate |
| 1-63 | 2'-(6-cyano-2-naphthyloxy)-5'-(3-chloro-4-methylbenzene sulfonyl)amino-4,5-dimethoxy-1,1'-biphenyl-2-carboxylic acid trifluoroacetate |
| 1-64 | 2'-(6-cyano-2-naphthyloxy)-5'-(2-toluylsulfonyl)amino-4,5-dimethoxy-1,1'-biphenyl-2-carboxylic acid trifluoroacetate |
| 1-65 | 2'-(6-cyano-2-naphthyloxy)-5'-methanesulfonylamino-4,5-dimethoxy-1,1'-biphenyl-2-carboxylic acid trifluoroacetate |
| 1-66 | 2'-(6-cyano-2-naphthyloxy)-5'-(3-fluoro-4-methoxybenzene sulfonyl)amino-4-(2-methylpropoxy)-1,1'-biphenyl-2-carboxylic acid trifluoroacetate |
| 1-67 | 2'-(6-cyano-2-naphthyloxy)-5'-(3-chloro-4-methylbenzene sulfonyl)amino-4-(2-methylpropoxy)-1,1'-biphenyl-2-carboxylic acid trifluoroacetate |
| 1-68 | 2'-(6-cyano-2-naphthyloxy)-5'-(2-toluylsulfonyl)amino-4-(2-methylpropoxy)-1,1'-biphenyl-2-carboxylic acid trifluoroacetate |
| 1-69 | 2'-(6-cyano-2-naphthyloxy)-5'-methanesulfonylamino-4-(2-methylpropoxy)-1,1'-biphenyl-2-carboxylic acid trifluoroacetate |

Example 1-34

2'-(6-amidino-2-naphthyloxy)-5'-(3,4-dimethoxybenzenesulfonyl)amino-1,1'-biphenyl-2-carboxylic acid trifluoroacetate

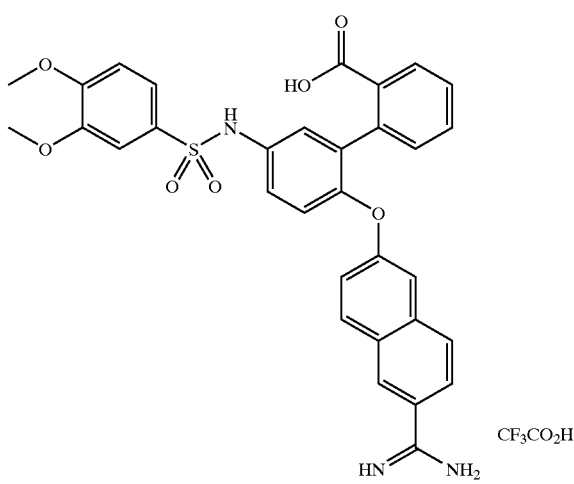

$^1$H-NMR (d$_6$-DMSO) δ: 3.73 (3H, s), 3.81 (3H, s), 6.98 (1H, d, J=9.2 Hz), 7.06–7.12 (5H, m), 7.15 (1H, dd, J=2.8, 9.2 Hz), 7.22 (1H, d, J=2.4 Hz), 7.29–7.34 (2H, m), 7.41 (1H, t, J=7.2 Hz), 7.68–7.71 (2H, m), 7.83 (1H, d, J=8.8 Hz), 7.92 (1H, d, J=9.2 Hz), 8.34 (1H, s), 9.04 (2H, brs), 9.31 (2H, brs), 10.10 (1H, s).

Example 1-40

2'-(6-amidino-2-naphthyloxy)-5'-(3-chloro-4-methylbenzenesulfonyl)amino-1,1'-biphenyl-2-carboxylic acid trifluoroacetate

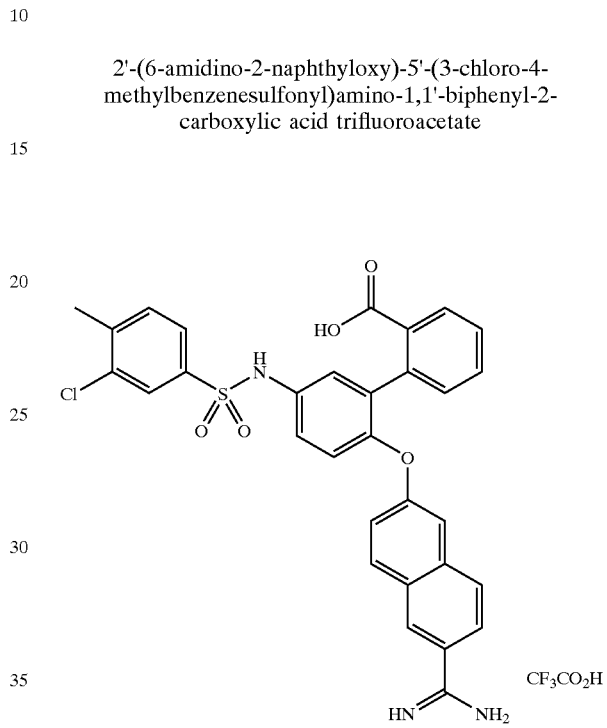

$^1$H-NMR (d$_6$-DMSO) δ: 2.38 (3H, s), 6.99–7.17 (6H, m), 7.32 (1H, t, J=7.6 Hz), 7.43 (1H, t, J=7.6 Hz), 7.57–7.59 (2H, m), 7.69–7.72 (3H, m), 7.84 (1H, d, J=8.8 Hz), 7.93 (1H, d, J=9.2 Hz), 8.34 (1H, s), 9.04 (2H, brs), 9.31 (2H, brs), 10.32 (1H, s).

Examples 2-1 to 2-4

The compound, (t-butyl 4-amino-2-(6-cyano-2-naphthyloxy)benzoate) obtained in a previous production example and sulfonyl chloride derivatives represented by the following formula (Ib):

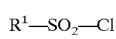

R$^1$—SO$_2$—Cl (where R$^1$ represents the respective R$^1$ groups in Table 19) were used for the same reaction as in Example 1-1 to obtain compounds for Examples 2-1 to 2-4, respectively.

TABLE 19

| EXAMPLE | Ar | R¹ | Y | $R_T$(min) | $(M+1)^+$ |
|---|---|---|---|---|---|
| 2-1 | naphthalene-2,6-diyl | 4-methoxyphenyl | COOH | 7.98 | 492.1 |
| 2-2 | ↑ | 4-fluorophenyl | ↑ | 8.15 | 480.2 |
| 2-3 | ↑ | 2-naphthyl | ↑ | 8.72 | 512.2 |
| 2-4 | ↑ | 3,4-dichlorophenyl | ↑ | 8.70 | 530.1 |

TABLE 20

| Example | Compound name |
|---|---|
| 2-1 | 2-(6-amidino-2-naphthyloxy)-4-(4-methoxybenzenesulfonyl)aminobenzoic acid trifluoroacetate |
| 2-2 | 2-(6-amidino-2-naphthyloxy)-4-(4-fluorobenzenesulfonyl)aminobenzoic acid trifluoroacetate |
| 2-3 | 2-(6-amidino-2-naphthyloxy)-4-(2-naphthalenesulfonyl)aminobenzoic acid trifluoroacetate |
| 2-4 | 2-(6-amidino-2-naphthyloxy)-4-(3,4-dichlorobenzenesulfonyl)aminobenzoic acid trifluoroacetate |

Examples 3-1 to 3-3

The compound (t-butyl 4-amino-2-(6-cyano-2-naphthyloxy)benzoate) obtained in a previous production example and acid chloride derivatives represented by the following formula (Ic):

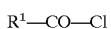

(where R¹ represents the respective R¹ groups in Table 21) were used for the same reaction as in Example 1-1 to obtain compounds for Examples 3-1 to 3-3, respectively.

TABLE 21

| EXAMPLE | Ar | R¹ | Y | $R_T$(min) | $(M+1)^+$ |
|---|---|---|---|---|---|
| 3-1 | naphthalene-2,6-diyl | 2-thienyl | COOH | 8.06 | 346.5 |

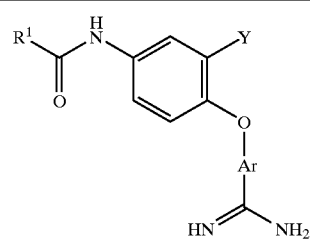

TABLE 21-continued

| EXAMPLE | Ar | R¹ | Y | R_T(min) | (M + 1)⁺ |
|---------|----|----|---|----------|----------|
| 3-2 | 1,4-phenylene | phenyl | 2-carboxyphenyl (COOH ortho) | 8.44 | 452.1 |
| 3-3 | 1,4-phenylene | ↑ | 3-carboxyphenyl (COOH meta) | 9.09 | 452.0 |

TABLE 22

| Example | Compound name |
|---------|---------------|
| 3-1 | 2-(6-amidino-2-naphthyloxy)-5-(2-thienylcarbonyl) aminobenzoic acid trifluoroacetate |
| 3-2 | 2'-(4-amidinophenoxy)-5'-benzoylamino-1,1'-biphenyl-2-carboxylic acid trifluoroacetate |
| 3-3 | 2'-(4-amidinophenoxy)-5'-benzoylamino-1,1'-biphenyl-3-carboxylic acid trifluoroacetate |

Examples 4-1 and 4-2

The compounds (t-butyl 5'-amino-2'-(4-cyanophenoxy)-1,1'-biphenyl-2-carboxylate and t-butyl 5'-amino-2'-(4-cyanophenoxy)-1,1'-biphenyl-3-carboxylate) obtained in previous production examples and acid anhydride derivatives represented by the following formula (Id):

$$(R^1-CO)_2O$$

(where $R^1$ represents the respective $R^1$ groups in Table 23) were used for the same reaction as in Example 1-1 to obtain compounds for Examples 4-1 and 4-2, respectively.

TABLE 23

| EXAMPLE | Ar | R¹ | Y | R_T(min) | (M + 1)⁺ |
|---------|----|----|---|----------|----------|
| 4-1 | 1,4-phenylene | isobutyl | 2-carboxyphenyl | 8.18 | 432.1 |

TABLE 23-continued

| EXAMPLE | Ar | R¹ | Y | $R_T$(min) | (M + 1)⁺ |
|---|---|---|---|---|---|
| 4-2 | (para-phenylene) | ↑ | (3-carboxyphenyl) | 8.71 | 432.1 |

TABLE 24

| Example | Compound name |
|---|---|
| 4-1 | 2'-(4-amidinophenoxy)-5'-(3-methylbutanoyl)amino-1,1'-biphenyl-2-carboxylic acid trifluoroacetate |
| 4-2 | 2'-(4-amidinophenoxy)-5'-(3-methylbutanoyl)amino-1,1'-biphenyl-3-carboxylic acid trifluoroacetate |

Example 5-1 2-(6-amidino-2-naphthyloxy)-5-[(3,4-methylenedioxybenzenecarbonyl)amino]benzoic acid trifluoroacetate

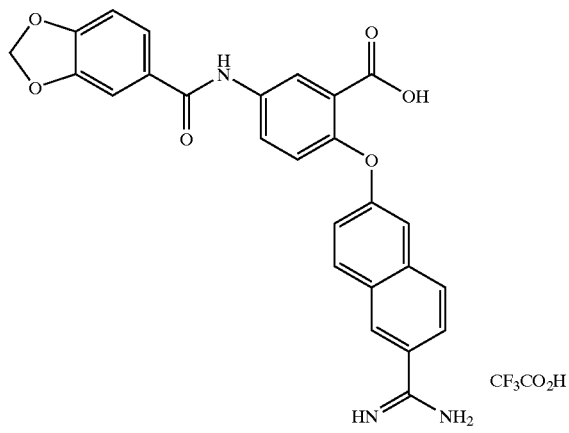

After adding 3,4-methylenedioxybenzenecarboxylic acid (9 mg), tetramethylfluoroformamidium hexafluorophosphate (14 mg) and DIEA (10 μl) to an N,N-dimethylformamide solution containing the compound (t-butyl 5-amino-2-(6-cyano-2-naphthyloxy)benzoate) (20 mg) obtained in a previous production example, reaction was conducted at 50° C. for 12 hours. The reaction solution was concentrated a saturated sodium bicarbonate solution was added to the residue, and extraction was performed with ethyl acetate. After freezing the aqueous layer with ethanol-dry ice, the ethyl acetate layer was decanted and the solvent was distilled off. Hydroxyamine hydrochloride (14 mg) and potassium carbonate (15 mg) were added to the obtained residue, and reaction was conducted for 12 hours at 60° C. in ethanol:water (2:1, 1 ml). After cooling to room temperature, the reaction solution was concentrated saturated saline was added to the residue, and extraction was performed with ethyl acetate. After freezing the aqueous layer with ethanol-dry ice, the ethyl acetate layer was decanted and the solvent was distilled off. The obtained residue was dissolved in acetic acid (1 ml), acetic anhydride (8 mg) was added and reaction was conducted at room temperature for 15 minutes. Next, 10% palladium-carbon (1 mg) was added thereto and catalytic reduction was carried out for 6 hours under ordinary pressure. The catalyst was then filtered off using celite, and the filtrate was concentrated. The residue was dissolved in trifluoroacetic acid-:dichloromethane (1:1, 1 ml) and reaction was conducted at room temperature for 90 minutes. The solvent was distilled off and the residue was purified by LC-MS (from 1% acetonitrile/water (0.1% trifluoroacetic acid) to 80% acetonitrile/water (0.1% trifluoroacetic acid), flow rate: 20 ml/min) to obtain 2-(6-amidino-2-naphthyloxy)-5-[(3,4-methylenedioxybenzenecarbonyl)amino]benzoic acid trifluoroacetate.

$R_T$=8.44 min, ESI-MS (m/z): 470.1 (M+1)⁺.

Examples 5-2 and 5-3

The compound (t-butyl 4-amino-2-(6-cyano-2-naphthyloxy)benzoate) obtained in a previous production example and carboxylic acid derivatives represented by the following formula (Ie):

R¹—COOH (where R¹ represents the respective R¹ groups in Table 25) were used for the same reaction as in Example 5-1 to obtain compounds for Examples 5-2 and 5-3, respectively.

TABLE 25

| EXAMPLE | Ar | R¹ | Y | R_T(min) | (M + 1)⁺ |
|---|---|---|---|---|---|
| 5-2 | 2,6-naphthyl | phenethyl | COOH | 8.73 | 454.2 |
| 5-3 | ↑ | 5-phenylpentyl | ↑ | 9.98 | 496.2 |

TABLE 26

| Example | Compound name |
|---|---|
| 5-2 | 2-(6-amidino-2-naphthyloxy)-5-(3-phenylbutanoyl)aminobenzoic acid trifluoroacetate |
| 5-3 | 2-(6-amidino-2-naphthyloxy)-5-(6-phenylhexanoyl)aminobenzoic acid trifluoroacetate |

Examples 6-1 to 6-3

The compound (t-butyl 5'-amino-2'-(6-cyano-2-naphthyloxy)-1,1'-biphenyl-2-carboxylate) obtained in a previous production example and isocyanate derivatives represented by the following formula (If):

$$R^1-NCO$$

(where R¹ represents the respective R¹ groups in Table 27) were used for the same reaction as in Example 1-1 to obtain compounds for Examples 6-1 to 6-3, respectively.

TABLE 27

| EXAMPLE | Ar | R¹ | Y | R_T(min) | (M + 1)⁺ |
|---|---|---|---|---|---|
| 6-1 | ↑ | 3-chlorophenyl | 2-carboxyphenyl | 9.41 | 517.0 |
| 6-2 | ↑ | 3-methoxyphenyl | ↑ | 9.49 | 547.0 |

TABLE 27-continued

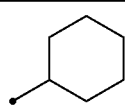

| EXAMPLE | Ar | R¹ | Y | $R_T$(min) | $(M + 1)^+$ |
|---|---|---|---|---|---|
| 6-3 | ↑ | (cyclohexyl) | ↑ | 9.47 | 523.1 |

TABLE 28

| Example | Compound name |
|---|---|
| 6-1 | 2'-(6-amidino-2-naphthyloxy)-5'-(3-chlorophenylureido)-1,1'-biphenyl-2-carboxylic acid trifluoroacetate |
| 6-2 | 2'-(6-amidino-2-naphthyloxy)-5'-(3-methoxyphenylureido)-1,1'-biphenyl-2-carboxylic acid trifluoroacetate |
| 6-3 | 2'-(6-amidino-2-naphthyloxy)-5'-(cyclohexylureido)-1,1'-biphenyl-2-carboxylic acid trifluoroacetate |

Example 7 t-Butyl 2-(6-amidino-2-naphthyloxy)-5-[(3,4-dichlorobenzenesulfonyl)amino]benzoate trifluoroacetate

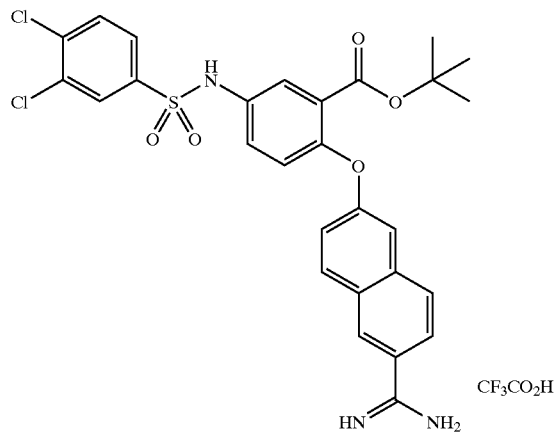

The compound (t-butyl 5-amino-2-(6-cyano-2-naphthyloxy)benzoate) obtained in a previous production example and 3,4-dichlorobenzenesulfonyl chloride instead of methanesulfonyl chloride, were used for treatment by the same method as in Example 2, except for omission of the step of hydrolysis of the ester with TFA, to obtain t-butyl 2-(6-amidino-2-naphthyloxy)-5-[(3,4-dichlorobenzenesulfonyl)amino]benzoate trifluoroacetate.

$R_T$=10.42 min, ESI-MS (m/z): 586.1 (M+1)⁺.

Example 8-1

2'-(6-amidino-2-naphthyloxy)-4-(2-methylpropyl carbamoyl)-5'-methanesulfonylamino-1,1'-biphenyl-2-carboxylic acid trifluoroacetate

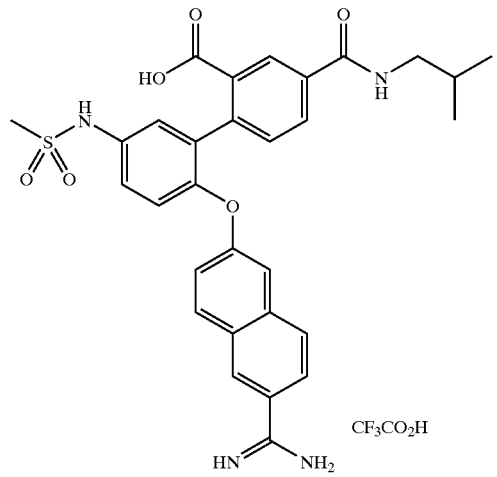

Methanesulfonyl chloride, (10 μL) was added to a pyridine solution (1 mL) containing the compound (methyl 5'-amino-2'-(6-cyano-2-naphthyloxy)-4-[(2-methylpropyl)carbamoyl]-1,1'-biphenyl-2-carboxylic acid) (20 mg) obtained in a previous production example, and the mixture was stirred at room temperature overnight. Nitrogen gas was sprayed into the reaction solution which was then concentrated. Ethyl acetate and saturated sodium bicarbonate water were added to the residue, and the organic layer was separated off. Next, nitrogen gas was sprayed into the organic layer which was then concentrated. A 1 N lithium hydroxide aqueous solution (0.4 mL), methanol (0.2 mL) and tetrahydrofuran (0.2 mL) were added to the residue, and the mixture was stirred at room temperature overnight. 1 N hydrochloric acid (0.4 mL) was then added to the reaction solution, extraction was performed with ethyl acetate, nitrogen gas was sprayed in and the solution was concentrated. Hydroxyamine hydrochloride (14 mg) and potassium carbonate (15 mg) were added to the obtained residue, and reaction was conducted for 12 hours at 60° C. in ethanol:water (2:1, 1 ml). After cooling to room temperature, the reaction solution was concentrated saturated saline was added to the residue, and extraction was performed with ethyl acetate. After freezing the aqueous layer with ethanol-dry ice, the ethyl acetate layer was decanted and the solvent was distilled off. The obtained residue was dissolved in acetic acid (1 ml), acetic anhydride (8 mg) was added and reaction was conducted at room temperature for 15 minutes. Next, 10% palladium-carbon (1 mg) was added thereto and catalytic reduction was carried out for 6 hours under ordinary pressure. The catalyst was then filtered off using celite, and the filtrate was concentrated. The residue was dissolved in trifluoroacetic acid:dichloromethane (1:1, 1 ml) and reaction was conducted at room temperature for 90 minutes. The solvent was distilled off and the residue was purified by LC-MS (from 1% acetonitrile/water (0.1% trifluoroacetic acid) to 80% acetonitrile/water (0.1% trifluoroacetic acid), flow rate: 20 ml/min) to obtain 2'-(6-amidino-2-naphthyloxy)-4-(2-methylpropylcarbamoyl)-5'-methanesulfonylamino-1,1'-biphenyl-2-carboxylic acid trifluoroacetate.

$R_T$=8.40 min, ESI-MS (m/z): 575.07 (M+1)$^+$.

Examples 8-2 to 8-4

The compound (methyl 5'-amino-2'-(6-cyano-2-naphthyloxy)-4-[(2-methylpropyl)carbamoyl]-1,1'-biphenyl-2-carboxylate) obtained in a previous production example and sulfonylchloride derivatives represented by the following formula (Ib):

$$R^1-SO_2-Cl$$

(where $R^1$ represents the respective $R^1$ groups in Table 29) were used for the same reaction as in Example 8-1 to obtain compounds for Examples 8-2 to 8-4, respectively.

TABLE 29

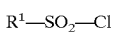

| EXAMPLE | Ar | $R^1$ | Y | $R_T$(min) | (M + 1)$^+$ |
|---|---|---|---|---|---|
| 8-2 | 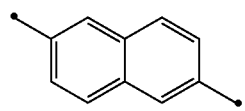 | 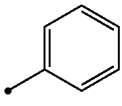 | 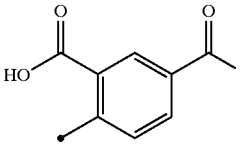 | 9.10 | 637.0 |
| 8-3 | ↑ | 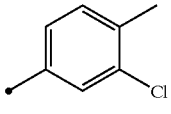 | ↑ | 10.10 | 685.1 |
| 8-4 | ↑ | 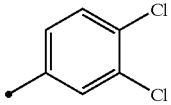 | ↑ | 10.10 | 705.0 |

TABLE 30

| Example | Compound name |
|---|---|
| 8-2 | 2'-(6-amidino-2-naphthyloxy)-4-(2-methylpropylcarbamoyl)-5'-benzenesulfonylamino-1,1'-biphenyl-2-carboxylic acid trifluoroacetate |
| 8-3 | 2'-(6-amidino-2-naphthyloxy)-4-(2-methylpropylcarbamoyl)-5'-(3-chloro-4-methylbenzenesulfonyl)amino-1,1'-biphenyl-2-carboxylic acid trifluoroacetate |
| 8-4 | 2'-(6-amidino-2-naphthyloxy)-4-(2-methylpropylcarbamoyl)-5'-(3,4-dichlorobenzenesulfonyl)amino-1,1'-biphenyl-2-carboxylic acid trifluoroacetate |

Example 9-1

2'-(6-amidino-2-naphthyloxy)-4-(2-methylpropyl carbamoyl)-4'-methyl-1,1'-biphenyl-2-carboxylic acid trifluoroacetate

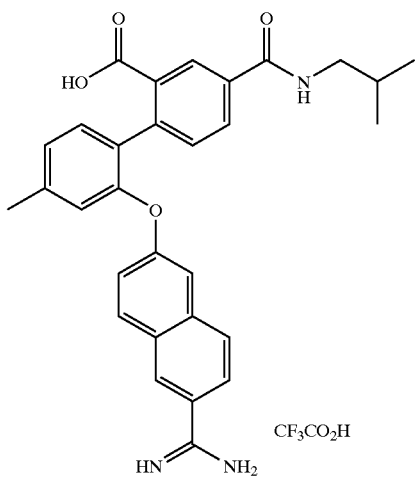

A 1 N lithium hydroxide aqueous solution (0.4 mL), methanol (0.2 mL) and tetrahydrofuran (0.2 mL) were added to the compound (methyl 2'-(6-cyano-2-naphthyloxy)-4-(2-methylpropylcarbamoyl)-4'-methyl-1,1'-biphenyl-2-carboxylate) (20 mg) obtained above, and the mixture was stirred at room temperature overnight. 1 N hydrochloric acid (0.4 mL) was added to the reaction solution, extraction was performed with ethyl acetate, and nitrogen gas was sprayed into the solution which was then concentrated. Hydroxyamine hydrochloride (14 mg) and potassium carbonate (15 mg) were added to the obtained residue, and reaction was conducted for 12 hours at 60° C. in ethanol:water (2:1, 1 ml). After cooling to room temperature, the reaction solution was concentrated saturated saline was added to the residue, and extraction was performed with ethyl acetate. After freezing the aqueous layer with ethanol-dry ice, the ethyl acetate layer was decanted and the solvent was distilled off. The obtained residue was dissolved in acetic acid (1 ml), acetic anhydride (8 mg) was added and reaction was conducted at room temperature for 15 minutes. Next, 10% palladium-carbon (1 mg) was added thereto and catalytic reduction was carried out for 6 hours under ordinary pressure. The catalyst was then filtered off using celite, and the filtrate was concentrated. The residue was dissolved in trifluoroacetic acid:dichloromethane (1:1, 1 ml) and reaction was conducted at room temperature for 90 minutes. The solvent was distilled off and the residue was purified by LC-MS (from 1% acetonitrile/water (0.1% trifluoroacetic acid) to 80% acetonitrile/water (0.1% trifluoroacetic acid), flow rate: 20 ml/min) to obtain the title compound.

$R_T$=9.20 min, ESI-MS (m/z): 496.3 (M+1)$^+$.

Example 9-2

2'-(4-amidino-2-phenoxy)-4-(2-methylpropyl carbamoyl)-4'-methyl-1,1'-biphenyl-2-carboxylic acid trifluoroacetate

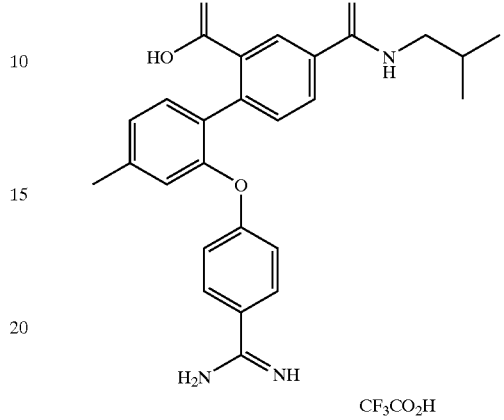

The compound (methyl 2'-(4-cyanophenoxy)-4-(2-methylpropylcarbamoyl)-4'-methyl-1,1'-biphenyl-2-carboxylate) obtained above was used for the same reaction as in Example 9-1 to obtain the title compound.

$R_T$=8.50 min, ESI-MS (m/z): 446.3 (M+1)$^+$.

TABLE 31

| Example | Compound name |
|---|---|
| 9-1 | 2'-(6-amidino-2-naphthyloxy)-4-(2-methylpropylcarbamoyl)-4'-methyl-1,1'-biphenyl-2-carboxylic acid trifluoroacetate |
| 9-2 | 2'-(4-amidino-2-phenoxy)-4-(2-methylpropylcarbamoyl)-4'-methyl-1,1'-biphenyl-2-carboxylic acid trifluoroacetate |

Pharmacological Activity Test (Inhibiting Activity Against Blood Clotting Factor VIIa)

Compounds of the present invention (Examples 1-4, 1-26, 1-39, 1-40 and 8-3) were each dissolved in dimethyl sulfoxide to 5 mg/ml, and then each solution was diluted 50-fold with reaction buffer to prepare a 100 µg/ml solution (2% dimethyl sulfoxide solution) Also, a 10-fold dilution series with reaction buffer was prepared with the compound solutions from 100 µg/ml to 1 ng/ml. Separately, dimethyl sulfoxide alone was diluted 50-fold with reaction buffer to prepare a 2% dimethyl sulfoxide solution as a control. The composition of the reaction buffer was 50 mM Tris-acetate (pH 7.5), 15 mM calcium chloride (CaCl$_2$), 0.15 M sodium chloride (NaCl) and 6 mg/ml Cephalin. There were also added to the buffer 10 nM human tissue factor (TF) and 5 nM human blood clotting factor VIIa, to prepare enzyme solutions. After separating off 65 µl of each solution, a 10 µl portion of the 2% dimethyl sulfoxide solution of each compound of the invention was added and preincubation was performed at room temperature. As a substrate there was added 25 µl of 1.0 mM Spectrozyme VII, and reaction was conducted for 40 minutes at room temperature. The enzyme reaction rate was quantified by the change ion absorbance of released 4-nitroanilide at 405 nm.

For measurement of the inhibiting activity against human blood clotting factor VIIa, the enzyme reaction rate was determined in the presence of the above-mentioned compounds of the present invention from 10 μg/ml to 0.1 ng/ml. The IC$_{50}$ values were calculated based on nonlinear regression analysis, as an index of the inhibiting activity against human blood clotting factor VIIa. The results are shown in Table 32.

TABLE 32

| Compound | IC50 (μM) |
|---|---|
| 1-4 | 1.43 |
| 1-26 | 0.21 |
| 1-39 | 0.03 |
| 1-40 | 0.04 |
| 8-3 | 0.004 |

As is clear from the results shown in Table 32, the novel amidino derivatives of the present invention were confirmed to exhibit excellent inhibiting activity against blood clotting factor VIIa.

According to the present invention it is possible to obtain novel amidino derivatives having serine protease inhibiting activity and especially excellent inhibiting activity against blood clotting factor VIIa, as well as their pharmacologically acceptable salts or solvates.

These amidino derivatives of the present invention and their pharmacologically acceptable salts or solvates are useful as prophylactic and/or therapeutic agents for clinical conditions involving thrombogenesis in which extrinsic clotting mechanisms are implicated and therefore the present invention provides blood clotting factor VIIa inhibitors, anticoagulants (particularly anticoagulants with inhibiting activity against blood clotting factor VIIa) and thrombosis therapeutic agents which are effective for prevention and/or treatment of clinical conditions involving thrombogenesis.

What is claimed is:

1. An amidino derivative represented by the following general formula (I):

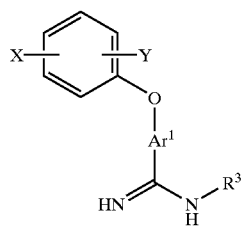

where X represents C$_{1-6}$ alkyl, a halogen atom, —NH$_2$ or a group represented by the following formula:

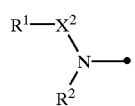

where R$^1$ represents optionally substituted C$_{1-6}$ alkyl, optionally substituted C$_{1-6}$ alkoxy, optionally substituted C$_{3-8}$ cycloalkyl, optionally substituted C$_{6-14}$ aryl, optionally substituted C$_{7-20}$ aralkyl, an optionally substituted 5- to 14-membered aromatic heterocyclic group or a group represented by the following formula:

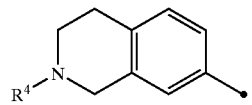

where R$^4$ represents hydrogen atom, C$_{1-6}$ alkyl or optionally substituted C$_{2-7}$ acyl), R$^2$ represents hydrogen atom or C$_{1-6}$ alkyl, and X$^2$ represents —CO—, —SO$_2$—, —NH—CO— or a single bond, R$^3$ represents hydrogen atom, hydroxyl, C$_{2-7}$ acyl or C$_{2-7}$ alkoxycarbonyl, Y represents a group of the formula —Ar$^2$—CO$_2$R$^5$ (where Ar$^2$ represents optionally substituted C$_{6-14}$ aryl, an optionally substituted 5- to 14-membered aromatic heterocyclic group or a single bond and R$^5$ represents hydrogen atom or C$_{1-6}$ alkyl), and Ar$^1$ represents 2,6-naphthylene, 1,4-phenylene, 1,3-phenylene, a group represented by the following formula:

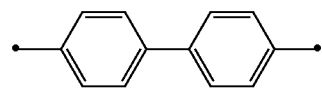

or a group represented by the following formula:

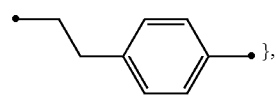

(where the ethyl end is linked to oxygen and the phenyl end is linked to amidine carbon);

or a pharmacologically acceptable salt or solvate thereof.

2. An amidino derivative or a pharmacologically acceptable salt or solvate thereof according to claim 1, wherein said amidino derivative is represented by the following general formula (II):

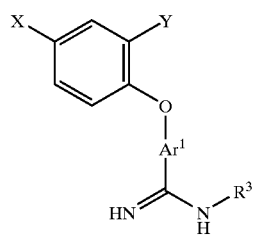

(where X, Y, Ar$^1$ and R$^3$ have the same definitions as X, Y, Ar$^1$ and R$^3$ in claim 1).

3. An amidino derivative or a pharmacologically acceptable salt or solvate thereof according to claim 1, wherein said amidino derivative is represented by the following general formula (III):

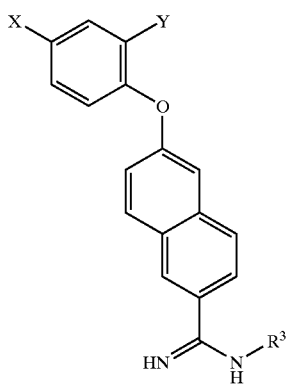

(where X, Y and $R^3$ have the same definitions as X, Y and $R^3$ in claim 1).

4. An amidino derivative or a pharmacologically acceptable salt or solvate thereof according to claim 1, wherein $R^3$ is hydrogen atom.

5. An amidino derivative or a pharmacologically acceptable salt or solvate thereof according to claim 1, wherein X is $C_{1-6}$ alkyl or a group represented by the formula $R^1$—$SO_2NH$— (where $R^1$ has the same definition as $R^1$ in claim 1).

6. An amidino derivative or a pharmacologically acceptable salt or solvate thereof according to claim 1, wherein X is a group represented by the formula $R^1$—$SO_2NH$— {where $R^1$ represents optionally substituted $C_{6-14}$ aryl or a group represented by the following formula:

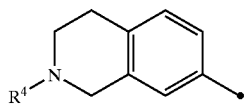

(where $R^4$ represents optionally substituted $C_{2-7}$ acyl)}.

7. An amidino derivative or a pharmacologically acceptable salt or solvate thereof according to claim 1, wherein Y is carboxyl or optionally substituted carboxyphenyl.

8. An amidino derivative or a pharmacologically acceptable salt or solvate thereof according to claim 1, wherein Y is a group represented by the following formula:

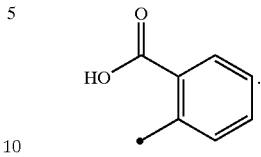

9. A blood clotting factor VIIa inhibitor comprising an amidino derivative or a pharmacologically acceptable salt or solvate thereof according to claim 1.

10. An anticoagulant containing, as an active ingredient, an amidino derivative or a pharmacologically acceptable salt or solvate thereof according to claim 1.

11. A thrombosis therapeutic agent containing, as an active ingredient, an amidino derivative or a pharmacologically acceptable salt or solvate thereof according to claim 1.

12. A method for inhibiting blood clotting factor VIIa, which involves administering an amidino derivative or a pharmacologically acceptable salt or solvate thereof according to claim 1.

13. A method for treating or preventing coagulation, which involves administering an amidino derivative or a pharmacologically acceptable salt or solvate thereof according to claim 1.

14. A method for treating or preventing thrombosis, which involves administering an amidino derivative or a pharmacologically acceptable salt or solvate thereof according to claim 1.

15. A treatment method for clinical conditions involving thrombogenesis in which extrinsic blood clotting mechanisms are implicated, which involves administering an amidino derivative or a pharmacologically acceptable salt or solvate thereof according to claim 1.

16. A prophylactic method for clinical conditions involving thrombogenesis in which extrinsic blood clotting mechanisms are implicated, which involves administering an amidino derivative or a pharmacologically acceptable salt or solvate thereof according to claim 1.

* * * * *